US007135175B2

(12) United States Patent
Castric

(10) Patent No.: US 7,135,175 B2
(45) Date of Patent: Nov. 14, 2006

(54) COMPOSITIONS AND METHODS FOR ELICITING AN IMMUNE RESPONSE TO GRAM-NEGATIVE BACTERIAL INFECTIONS

(75) Inventor: Paul A. Castric, Pittsburgh, PA (US)

(73) Assignee: Duquesne University of the Holy Ghost, Pittsburgh, PA (US)

( * ) Notice: Subject to any disclaimer, the term of this patent is extended or adjusted under 35 U.S.C. 154(b) by 26 days.

(21) Appl. No.: 11/192,962

(22) Filed: Jul. 29, 2005

(65) Prior Publication Data

US 2006/0057700 A1 Mar. 16, 2006

(51) Int. Cl.
*A61K 39/00* (2006.01)
*A61K 39/02* (2006.01)
*A61K 39/38* (2006.01)
*A61K 39/395* (2006.01)

(52) U.S. Cl. .............................. 424/130.1; 424/234.1; 424/242.1; 424/184.1

(58) Field of Classification Search ............ 424/130.1, 424/184.1, 234.1, 242.1
See application file for complete search history.

(56) References Cited

U.S. PATENT DOCUMENTS

| | | | |
|---|---|---|---|
| 5,288,617 | A | 2/1994 | Mattick et al. |
| 5,494,672 | A | 2/1996 | Hodges et al. |
| 5,612,036 | A | 3/1997 | Hodges et al. |
| 5,698,198 | A | 12/1997 | Young |
| 5,804,198 | A | 9/1998 | Lindberg et al. |
| 5,874,088 | A | 2/1999 | Mekalanos |
| 5,994,072 | A | 11/1999 | Lam |
| 6,872,398 | B1 | 3/2005 | Castric |

FOREIGN PATENT DOCUMENTS

| | | |
|---|---|---|
| EP | 81107234.7 | 3/1982 |
| WO | WO 86/072557 | 5/1986 |
| WO | WO 92/12169 | 7/1990 |
| WO | WO90/11777 | 10/1990 |
| WO | WO 90/13563 | 11/1990 |
| WO | WO 93/11791 | 6/1993 |
| WO | WO 97/23600 | 12/1996 |

OTHER PUBLICATIONS

Peter Castric, piLO, a gene required for glycosylation of Pseudomonas aeruginosa 1244 pilin, 1995, Microbiology, 141:1247-1254.

Castric et al., Structural Characterization of the Pseudomonas aeruginosa 1244 Pilin Glycan, Journal of Biological Chemistry, vol. 276, No. 28, pp. 26479-26485, 2001.

Maurer, J.J. et al, Development of Primers to O-Antigen Biosynthesis Genes for Specific Detection of Escherichia Coli O157 by PCR, Applied and Environmental Microbiology, Jul. 1999, vol. 65, No. 7, pp. 2954-2960.

Goldberg, J.B., et., Cloning and Surface Expression of Pseudomonas Aeruginosa O-Antigen in Escherichia Coli, Proceedings of National Academy of Science, USA, Nov. 1992, vol. 89, pp. 10716-10720.

Burrows, L.L. et al., Molecular Characterization of the Pseudomonas Aeruginosa Serototype 05 B-Band lipopolysaccharide gene cluster, Molecular Micribiology 1996, 22 (3), pp. 481-495.

Belanger, M. et al. 1999, Functional Analysis of genes responsible for synthesis of B-Band O-antigen of Pseudomonas aeruginosa serotype 06 lipopolysaccharide, Microbiology, pp. 3505-3521.

Lisa Saiman et al.,Cross-Reactivity of Pseudomonas aeruginosa Antipilin Monoclonal Antibodies with Heterogeneous Strains of P. aeruginosa and Pseudomonas cepacia, Infection and Immunity, Sep. 1989, vol. 57, No. 9, pp. 2764-2770.

Power et al., Genetic characterization of pilin glycosylation in Neisseria meningitis, Apr. 2000, vol. 146 (Pt. 4), 967-979.

Maniatis, Fritsch & Sambrook, Molecular Cloning: A Laboratory Manual (1982).

DNA Cloning, vol. I & II, (D.N. Glover, ed. 1985).

Antonio Di Giandomenico, Masters Thesis, Identification of the Pilin Glycan Source in Pseudomonas aeruginosa 1244 and Implications on PilO Substrate Specificity. Master of Science in Biology, Jul. 20, 2001.

Woods et al., Role of Pili in Adherence of Pseudomonas aeruginosa to Mammalian Buccal Epithelial Cells, Sep. 1980, 1146-1151, vol. 29, No. 3.

Hatano and Pier, Complex Serology and Immune Response of Mice to Variant High-Molecular Weight O Polysaccharides Isolated from Pseudomonas aeruginosa Serogroup O2 Strains, Infection and Immunity, vol. 66, No. 8, Aug. 1998, 3719-3726.

*Primary Examiner*—Mark Navarro
(74) *Attorney, Agent, or Firm*—Eckert Seamans Cherin & Mellott, LLC; Arnold B. Silverman

(57) ABSTRACT

Compositions for eliciting an immune response against Gram-negative bacterial infections and methods of making such compositions are provided. The composition comprises glycosylated pilin, the pilin being glycosylated with the O-antigen of a target Gram-negative bacteria of interest. Methods of eliciting an immune response by administration of such compositions are also provided.

10 Claims, 20 Drawing Sheets
(20 of 20 Drawing Sheet(s) Filed in Color)

MAb: 11.14 5.44

SEQUENCE LISTING

```
<160> NUMBER OF SEQ ID NOS: 8

<210> SEQ ID NO 1
<211> LENGTH: 40
<212> TYPE: DNA
<213> ORGANISM: Artificial
<220> FEATURE:
<223> OTHER INFORMATION: Description of Artificial Sequence: Primer

<400> SEQUENCE: 1

gccgtcgtga attcggtacc agcgaataag gtactaagcc                     40


<210> SEQ ID NO 2
<211> LENGTH: 39
```

-continued

<212> TYPE: DNA
<213> ORGANISM: Artificial
<220> FEATURE:
<223> OTHER INFORMATION: Description of Artificial Sequence: Primer

<400> SEQUENCE: 2
gctacgcctt cgaacttgct gccgttcgag atacttctc 39

<210> SEQ ID NO 3
<211> LENGTH: 25
<212> TYPE: DNA
<213> ORGANISM: Artificial
<220> FEATURE:
<223> OTHER INFORMATION: Description of Artificial Sequence: Primer

<400> SEQUENCE: 3
gttcgtgccg cacttcaagc cgggc 25

<210> SEQ ID NO 4
<211> LENGTH: 25
<212> TYPE: DNA
<213> ORGANISM: Artificial
<220> FEATURE:
<223> OTHER INFORMATION: Description of Artificial Sequence: Primer

<400> SEQUENCE: 4
tcagggttct cgccgcctct ggcga 25

<210> SEQ ID NO 5
<211> LENGTH: 25
<212> TYPE: DNA
<213> ORGANISM: Artificial
<220> FEATURE:
<223> OTHER INFORMATION: Description of Artificial Sequence: Primer

<400> SEQUENCE: 5
gctgccttcg accaagaagc ggttg 25

<210> SEQ ID NO 6
<211> LENGTH: 25
<212> TYPE: DNA
<213> ORGANISM: Artificial
<220> FEATURE:
<223> OTHER INFORMATION: Description of Artificial Sequence: Primer

<400> SEQUENCE: 6
ggagtaggtg gctacgtctc cgaac 25

<210> SEQ ID NO 7
<211> LENGTH: 46
<212> TYPE: DNA
<213> ORGANISM: Artificial
<220> FEATURE:
<223> OTHER INFORMATION: Description of Artificial Sequence: Primer

<400> SEQUENCE: 7
gccgaagata acgtagctgt tcgaagggcg gtcgaacgaa gggctg 46

<210> SEQ ID NO 8
<211> LENGTH: 49
<212> TYPE: DNA
<213> ORGANISM: Artificial

-continued

```
<220> FEATURE:
<223> OTHER INFORMATION: Description of Artificial Sequence: Primer

<400> SEQUENCE: 8

gtcagccgag gctacgcctt cgaacttgct gccgttcgag atacttctc          49
```

COMPOSITIONS AND METHODS FOR ELICITING AN IMMUNE RESPONSE TO GRAM-NEGATIVE BACTERIAL INFECTIONS

GOVERNMENT CONTRACT

This work was supported in part by the National Institutes of Health, U.S. Department of Health and Human Services under Contract No. R15 AI43317. The Government may have certain rights in this invention.

CROSS REFERENCE TO RELATED APPLICATIONS

This application claims the benefit of U.S. application Ser. No. 10/085,862, filed Feb. 27, 2002, which claims the benefit of U.S. application Ser. No. 10/047,159, filed Jan. 14, 2002, which are incorporated herein by reference.

FIELD OF THE INVENTION

The present invention relates generally to compositions for eliciting an immune response against Gram-negative bacterial infections, methods of making such compositions, and methods of eliciting an immune response by administration of such compositions.

BACKGROUND INFORMATION

Bacterial sepsis and related septic shock are frequently lethal conditions caused by infection which can result from surgery, trauma, and immune suppression related to cancer, transplantation therapy or other diseases. Gram-negative bacterial infections comprise the most serious infectious disease problem seen in hospitals today, now counting for thousands of infections yearly with a high overall mortality.

In prior decades, most infectious diseases contracted in hospitals were attributable to acute Gram-positive bacterial pathogens such as *Staphylococcus* and *Streptococcus*. However, in the last thirty years the incidence of nosocomial infections with *Escherichia coli, Pseudomonas aeruginosa* and other Gram-negative bacteria has risen steadily. The increase has been attributed to advances in medical treatment, resulting in prolonged survival of immunologically impaired hosts and the increased prevalence of wide spread antibiotic use in the hospital environment.

In addition to individuals receiving anti-cancer chemotherapy or immunosuppressive treatments following organ or tissue transplants, other individuals significantly at risk for Gram-negative bacterial infections include those with cystic fibrosis (CF) and burn victims. More than 90% of mortality in CF patients is the result of *P. aeruginosa* infections. Infections in immuno-compromised hosts typically exhibit resistance to many antibiotics, or develop resistance over the long course of the infection, making conventional treatment difficult. Natural selection for drug resistant bacteria by the extensive use of antibiotics has contributed to a Gram-negative bacteria involving into pathogens of major clinical significance.

A variety of factors contribute to the pathogenicity of Gram-negative bacteria. As described above, many Gram-negative bacteria are highly resistant to antibiotics. Additionally, many Gram-negative bacteria synthesize cellular and extra-cellular products to ensure infection of their hosts. Cellular products include lipopolysacciaride (LPS), pili, and alginate (in *P. aeruginosa*), a mucoid polysaccharide that is thought to protect the bacteria from phagocytosis. LPS is produced in a variety of forms, is highly immunogenic, mediates entry into eukaryotic cells and protects the bacteria from host defensives.

The LPS of *P. aeruginosa* and other Gram-negative bacteria is made up of a conserved structure that is widely shared among diverse Gram-negative bacterial genera. The core structure is comprised of three regions: (1) an O-antigen (O-polysaccharide comprised of repeating units of 3–5 sugars); (2) an inner and outer core; and (3) a lipid A region. The O-antigen is attached to the lipid A via the core region, and the lipid A portion is imbedded into the outer membrane of the organism where it serves as an anchor for the LPS. *P. aeruginosa* usually expresses two distinct types of LPS on its outer membrane, A-band and B-band. B-band LPS is the immunodominant antigen and is used to divide the organism into serogroups and subgroups. This is also seen in some other Gram-negative bacteria having LPS.

The lipid A portion of the LPS consists of short phosphorylated lipids acylated to a glucosamine disaccharide backbone and is thought to be the most toxic portion of the LPS. Also known as endotoxin A, it can overinduce the inflammatory response of the immune system, resulting in septic shock or even death. Septic shock causes a decrease in blood pressure, which can cause harm to the kidneys, lungs and gastrointestinal tract.

Pili are also an important virulence factor. Pili are hair-like fibers that extend outward from the bacterial cell and allow the bacteria to interact with surfaces, and are believed to be responsible for initial attachment of the bacteria to host cells. Without the ability to attach to host cells, bacteria are much less virulent. For example, Woods et al. (1980) demonstrated that the use of homologous anti-pilus antisera prevented attachment to buccal epithelial cells in challenge assays.

It has been shown that *P. aeruginosa* pilus is glycosylated (Castric, 1995, Microbiology, 141: 1247–1254); other type IV pilin bacteria are thought to be glycosylated as well. Structural analysis (Castric, et al., *Journal of Biological Chemistry,* 276:26479–26485) has shown that the pilin glycan is a trisaccharide that is identical to the O-antigen repeating unit of this microbe, and originates from the O-antigen biosynthetic pathway (unpublished observations). The pilin glycan is a major B-cell epitope of the pilus. Subcutaneous immunization of mice with pure glycosylated *P. aeruginosa* 1244 pili produced glycan (O-antigen)-specific antibodies. These antibodies recognized LPS from *P. aeruginosa* 1244 as determined by ELISA and Western blot (unpublished results). In addition, intranasal immunization of mice with glycosylated pili stimulated production of LPS-specific IgA in bronchial lavage and protected the animals against challenge with *P. aeruginosa* 1244. These results indicate that the *P. aeruginosa* pilin glycan produces an anti-LPS response.

Attachment of the O-antigen repeating unit to the pilus requires a functioning pilO gene (Castric, 1995, *Microbiology,* 141:1247–1254); the pilO protein in *P. aeruginosa* 1244 has been found to be extremely non-specific as to O-antigen repeating unit. For example (and as described more fully in the examples below), the gene cluster that codes for synthesis of the *Escherichia coli* O157 O-antigen was cloned in a broad-host-range cosinid and produced O157 LPS in *P. aeruginosa* 1244. The pilin sub-units produced by this strain were glycosylated with either O157 antigen or the host cell repeating unit (demonstrated in the examples presented below). This same nonspecificity was seen with a cloned heterologous *P. aeruginosa* O-antigen gene cluster.

As identified in numerous studies, the O-antigen repeating unit of LPS is the principal target of the immune response. However, developing a heterologous vaccine to O-antigens from multiple strains has proven difficult. For example, a study on the immune response in mice to high molecular weight O-antigens was performed with *P. aeruginosa* serogroup O2 strains (O2a–O2f). homologous O-antigens were more immunogenic in low doses, and elicited highly protective opsonic antibodies (Hatano and Pier, 1998). When vaccination was given as heterologous O-antigens, antibodies were generated to all strains, but cross-reactive opsonic antibodies were decreased, rather than enhanced among the strains tested (Hatano and Pier, 1998).

The use of an LPS-based vaccine has serious drawbacks, as this type of vaccine includes the toxic part (lipid A) of the LPS molecule, as well as the drawbacks discussed above regarding multivalent vaccines. There is a continued need for the development of compositions for eliciting an immune response in a vertebrate animal to Gram-negative bacterial infections, to assist the native immune response in overcoming such infections.

SUMMARY OF THE INVENTION

The present invention provides a method of producing glycosylated pilin comprising introducing a vector containing the genes required for biosynthesis of the O-antigen repeating unit of a Gram-negative bacterium into *P. aeruginosa*. When these genes are expressed in *P. aeruginosa*, pili produced by this organism will become glycosylated with the desired O-antigen repeating unit of the target Gram-negative bacterium. The glycosylated pili can then be isolated and used in a composition and administered to a vertebrate animal to elicit an immune response against the O-antigen of the target Gram-negative bacterium. Significantly, handling of the pathogen is not required (other than to clone the O-antigen gene cluster) in the production of this vaccine. Using the methods of the present invention, O-antigen pathway genes can be cloned and expressed in *P. aeruginosa* where they will produce the glycan for pilin glycosylation.

In an additional aspect of the present invention, the O-antigen repeating unit can be isolated from the purified glycosylated pili. This molecule can be attached to a carrier protein, using chemical methods known in the art. O-antigen repeating units from one or more different Gram-negative bacteria of interest can be simultaneously attached to a carrier protein, or to glycosylated pili, to produce a multivalent composition.

True pili, protein fibers extending from the cell surface, are found only in certain species of Gram-negative bacteria. Pili have been divided into several classes, one of which is referred to as type IV. Type IV pili are characterized by 1) their ability to extend and retract; 2) their cellular location (they are usually found in clusters, usually at the cell pole); and 3) the pilin sub-units have a characteristic sequence structure (constant N-terminal and a variable C-terminal regions). Many important Gram-negative pathogenic bacteria produce type IV pili, such as *Neisseria meningitidis, N. gonorrhoeae, Vibro cholerae*, certain *Escherichia coli* strains, *Moraxella* species and *Legionella* species.

In the method described in copending U.S. patent application Ser. No. 09/337,393, the gene (denoted as the pilA gene) encoding structural information for a pilin which was the desired immunogenic target, as well as the gene encoding the protein which glycosylates pilin (the pilO gene) were cloned into a Gram-negative bacteria which was able to produce type IV pilin. Using the host bacterium's own pilin assembly mechanisms, the pilin of interest would be glycosylated, via pilO, with the O-antigen repeating unit of the host bacterium. Thus this method required the use of host bacteria having pilin assembly mechanisms, namely type IV pili-producing bacteria, and was limited to the production of glycosylated pilin having O-antigens from these pilin-producing bacteria only.

However, most Gram-negative pathogens do not produce type IV pili. This includes pathogens from the following genera: *Salmonella, Shigella, Hemophilus, Bordetella, Yersinia, Francisella, Brucella, Burkholderia, Bartonella, Pasteurella, Proteus*, and *Providencia*. Other Gram-negative pathogens that do not produce type VI pili are the rickettsia (including coxiella species) and the coliform bacilli (including many *E. coli* strains). Thus, the present invention provides a method of attaching O-antigens of many more species of bacteria to pilin of *P. aeruginosa*, than was previously possible with prior art methods. Recent advances in the ability to clone the O-antigen gene cluster from various Gram-negative bacteria now allows the design of vaccines specific for different strains of Gram-negative bacteria, including those which could not previously be targeted with prior methods. Because the *P. aeruginosa* pilO protein has been demonstrated to be non-specific as to substrate, it is anticipated that the O-antigen from virtually any Gram-negative bacteria can be attached to a *P. aeruginosa* pilin.

Further benefits of the present invention are derived from the nature of the immune response evoked when single O-antigen repeating units are attached to a pilin or other carrier protein. A covalent linkage of this glycan to pilin or other protein gives a stronger, longer lasting immune response because a T-cell-dependent process is evoked (as compared with the T-cell independent response evoked by LPS or detached O-antigen polysaccharide). When the O-antigen repeating unit is attached to pilin or other carrier protein, the size, orientation and organization of the epitope is different from that found on LPS, in which the O-antigen repeating units are arranged in chains. It is thought that the smaller O-antigen size evokes a stronger immune response. In addition, a smaller epitope can provide more interaction with B-cells per vaccine dose. Of particular significance is the availability of the O-antigen repeating unit terminal sugar residue in high molar ratio. The free terminal residue is only present once in each LPS or O-antigen polysaccharide.

Purity and processing are also improved in the present invention. For example, in addition to the absence of lipid A, glycosylated pili contain no contaminating protein or nucleic acids often found in LPS preparations. There is no LPS core present, so that only the target antigen is delivered, thus avoiding immune suppression problems. Additionally, no acid treatment is required, as is used in O-antigen polysaccharide production, which results in the destruction of certain O-antigens.

Importantly, using the methods of the present invention, glycan epitopes are amenable to engineering. For example, it is possible to produce pilins or carrier proteins having specific desired combinations of glycans from more than one source; epitopes that are most effective can be identified and used in a composition to elicit an immune response. These epitopes can be selectively bound to pilin or other carrier proteins so that they have derived epitopes which are not structurally similar, thus overcoming antigenic suppression problems seen in earlier multivalent LPS vaccines.

LPS purification is time consuming, expensive and difficult; glycosylated pili can be produced in large amounts either from broth cultures or solid media. Purification of glycosylated pili is quickly accomplished, inexpensive and requires only common laboratory procedures.

It is an object of the present invention, therefore, to provide a method of producing glycosylated pilin, wherein the pilin is glycosylated with the O-antigen of a Gram-negative bacteria of interest.

It is an additional object of the present invention to provide a composition comprising glycosylated pilin.

It is an additional object of the present invention to provide a composition comprising glycosylated pilin, which can be administered to a vertebrate animal to provide resistance to bacterial infection.

It is an additional object of the present invention to provide a method of eliciting an immune response in a vertebrate animal, by administration of a composition comprising glycosylated pilin.

It is an additional object of the present invention to provide isolated O-antigen repeating unit strictures, which can be bound to pilin or other carrier proteins for use in a vaccine or in diagnostic kits to detect the presence of infection.

These and other objects of the invention will become more readily apparent from the following detailed description, examples and appended claims.

BRIEF DESCRIPTION OF THE DRAWINGS

The file of this patent contains at least one drawing executed in color. Copies of this patent with color drawings will be provided by the Patent and Trademark Office upon request and payment of the necessary fee.

The invention is further illustrated by the following non-limited drawings in which.

DETAILED DESCRIPTION OF PREFERRED EMBODIMENTS

Figure 1:
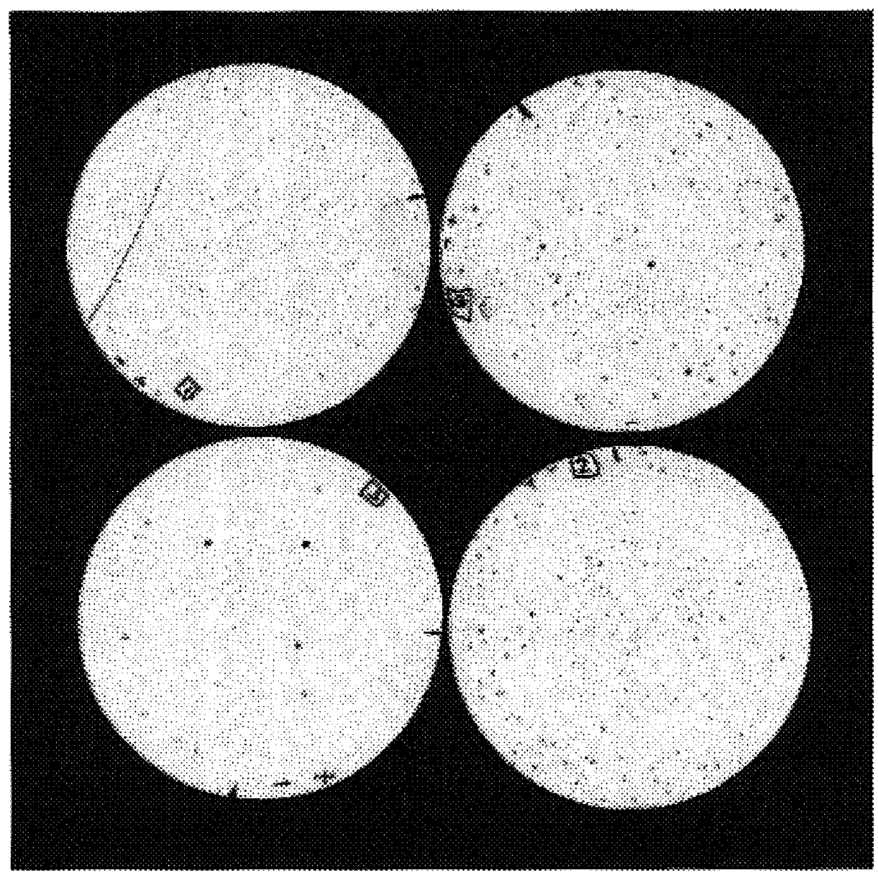
FIG. 1 shows colony immunoblots of *E. coli* HB101 transduced with pDS300 library subcloned into pLAFR1. A partial digestion of pDS300 into 30 Kb segments was performed as described by Maniatis (1987) and cloned into EcoR I treated pLAFR1. This DNA was packaged as bacteriophage lambda particles and used to transduce *E. coli* HB101. Colonies were lifted by placing a 0.45 μm nitrocellulose membrane directly on to each plate. Each immunoblot was reacted wraith *E. coli* O157:H7 antiserum. A red color indicates a positive reaction.

The present invention provides a method of producing glycosylated pilin comprising introducing a vector containing genes encoding an O-antigen of a Gram-negative bacterium into a strain of *P. aeruginosa* containing the pilO gene. The O-antigen is expressed in *P. aeruginosa* and pilin is glycosylated with the O-antigen of said Gram-negative bacterium. The glycosylated pilin can then be isolated. Preferably, strain 1244 of *P. aeruginosa* is used, although other strains having the pilO gene are also suitable and contemplated as within the scope of the present invention.

Gene clusters for the biosynthesis of core O-oligosaccharides and O-antigens have been cloned and characterized from several bacterial species, including some from nonenteric genera such as *Bordetella, Haemophilus, Neisseria, Vibrio, Amormutharia*, and *Xanthomonas*. See, e.g., U.S. Pat. No. 5,994,072 and references cited therein, which discuss isolation of O-antigen gene clusters in *P. aeruginosa* and other species. See also 1) Maurer, J. J. et al. 1999. Development of Primers to O-antigen Biosynthesis Genes for specific Detection of *Escherichia coli* 0157 by PCR. *Appl Environ Microbiol.* 65:2954–2960; 2) Goldberg, J. B. et al. 1992. Cloning and surface expression of *Pseudomonas aeruginosa* O-antigen in *Escherichia coli. Proc Natl Acad Sci, USA.* 89:10716–10720; 3) Burrows, L. L. et al. 1996. Molecular characterization of the *Pseudomonas aeruginosa* O5 (*P. aeruginosa* O1) B-band lipopolysaccharide gene cluster. *Mol Microbiol.* 22:481–495; and 4) Belanger, M. L. et al. 1999. Functional analysis of genes responsible for synthesis of B-band O-antigen of *Pseudomonas aeruginosa* serotype O6. *Microbiology.* 145:3505–3521. These references provide additional descriptions of methods of isolating the O-antigen gene cluster.

Using methods known in the art, the gene cluster for the target O-antigen of the target Gram-negative bacteria can be isolated and cloned into a suitable vector. Preferably, the target Gram-negative bacteria will be *P. aeruginosa* or *E. coli*, although other Gram-negative bacteria are contemplated as within the scope of the present invention.

Any suitable vector known in the art can be used. Suitable vectors include, for example, the pLAFR1 vector (Friedman, et al. 1982 Gene 18 289–286) or the pIJ2300 vector (Liu, et al., 1990 Mol. Gen. Genet. 220 433–440). Promoters found within the O-antigen gene cluster will sufficiently regulate expression of the gene; hyperexpression is not necessary. The vector containing the O-antigen gene cluster is expressed in *P. aeruginosa*, and the pilin glycosylation proteins are able to add subunits of the O-antigen repeating unit from the target bacterium to the core pilin, producing glycosylated pilins which can be isolated for use in providing resistance to bacteria infection and in diagnostic assays. For example, the plasmid pDIG4, described below in Materials and Methods, containing the O-antigen gene cluster from *E. coli* O157:H7 was placed into the broad host range expression vector pLAFR1. The O-antigen was expressed, and pili produced by *P. aeruginose* were glycosylated with the O-antigen from the *E. coli*. Please see e.g., Maniatis, Fitsch and Sambrook, *Molecular Cloning; A Laboratory Manual* (1982) or *DNA Cloning* Volumes I and II (D. N. glover ed. 1985) for general cloning methods.

The glycosylated pili of the present invention are isolated using methodology well known in the art or by a new large scale production method described in a co-pending application, U.S. patent application Ser. No. 09/337,393, expressly incorporated herein by reference. The glycosylated pili can be used in a composition for providing resistance against infection with the host bacteria or as a diagnostic tool for detection of host bacterial infection. Glycosylated pili containing O-antigen repeating units from different sources can be mixed together to provide a multivalent composition capable of eliciting an immune response to a variety of strains or species, rather than a single strain.

In an additional aspect of the present invention, the O-antigen repeating unit structure can be further isolated from the isolated glycosylated pilin. Complete proteolysis of the purified glycosylated pilin releases the glycan covalently attached to a serine residue (the pilin residue to which it was attached). The aminoglycan can be purified by gel filtration and thin layer chromatography. Such isolated aminoglycan can be covalently attached by chemical methods known to one skilled in the art, to a carrier protein. For example, the aminoglycan can be attached to ovalbumin or other suitable carrier protein such as keyhole limpet hemocyanin, and exotoxin A toxoid using the following method: after dissolving the carrier protein in a phosphate buffer solution (PBS), the aminoglycan is added, after which 0.2% glutaraldehyde in PBS is added dropwise. The solution is stirred for one hour at room temperature, at which time glycine is added to quench the cross-linking reaction. The mixture is dialyzed and can be stored frozen. Aminoglycans from one or more different Gram-negative bacteria can be attached to the same carrier protein, or to glycosolated pilin, resulting in a multivalent composition for use in eliciting an immune response. Alternatively, compositions with different O-antigens on different carrier proteins can be prepared, to reduce adverse reactions brought on by the carrier.

Any of the purified solutions described above are prepared for administration to vertebrate animals by methods known in the art, which can include filtering to sterilize the solution, diluting the solution, adding an adjuvant and stabilizing the solution. The composition can be lyophilized to produce a dried form for ease in transportation and storage. Further, the composition may be prepared in mixed form which contains the glycosylated pili, mixed glycosylated pili or carrier protein having one or more different glycans attached, as described above, with at least one other antigen, as long as the added antigen does not interfere with the effectiveness of the composition and the side effects and adverse reactions are not increased additively or synergistically.

In a further aspect of the present invention, the isolated glycosylated pilin or isolated aminoglycan can be used to test vertebrates suffering from infection for the presence of antibodies indicating the presence of an immune response. Using standard methodology well known in the art, a diagnostic assay can be constructed by coating on a surface (i.e. a solid support), for example a microtitration plate or a nitrocellulose or other membrane, all or a unique portion of the glycosylated pili, carrier protein containing the O-antigen repeating unit, or the isolated O-antigen repeating unit structure itself, and contacting it with the serum of an animal suspected of having a Gram-negative bacterial infection. The presence of a resulting complex formed between glycosylated pilin or aminoglycan and antibodies specific therefor in the serum can be detected by any of the known methods common in the art, such as fluorescent antibody spectroscopy or colorimetry. This method of detection can be used, for example, for the diagnosis and typing of Gram-negative bacterial infections. Additionally, purification of anti-LPS antibodies can be carried out by covalently attaching the aminoglycan to a gel matrix (i.e., dextran). Using affinity chromatography, antibodies from the sera of immunized vertebrate animals can be isolated and purified.

As used herein, the term "vertebrate animal" refers to any vertebrate member of the animal kingdom, including mammals (including humans), birds, reptiles, amphibians and fishes.

As used herein, the phrase "eliciting an immune response" refers to, for example, the ability of the methods and compositions of the present invention to elicit an antibody response. The antibodies so elicited may be purified by methods known in the art and used in clinical or environmental settings, using techniques such as ELISA, Western blot or surface plasmon resonance to allow rapid identification of the organism present in a vertebrate animal suffering from a Gram-negative bacteria infection.

Additionally, these antibodies can be used as an antiserum and administered to vertebrate animals in a suitable carrier to provide passive resistance to a Gram-negative bacterial infection and assist the animal's native immune response in fighting the infection.

In an additional aspect of the present invention, "eliciting an immune response" refers to the ability of the glycosylated pili or glycosylated carrier protein, when administered to a vertebrate animal in a suitable carrier, to provide protective immunity.

The composition may be stored in a sealed vial, ampule or the like. The present composition can generally be administered in the form of a liquid or suspension. In the case where the composition is in a dried form, the composition is dissolved or suspended in sterilized distilled water before administration. Generally, the composition may be administered orally, subcutaneously, intradermally or intramuscularly. In the case of respiratory infection, the preferred route of administration is intranasal, in a dose effective for the production of neutralizing antibody and providing resistance from infection or disease.

EXAMPLES

The following examples are intended to illustrate the invention and should not be construed as limiting the invention in any way.

Materials and Methods

A. Media and Conditions

All cultures were grown in LB (Luria Bertani) broth or on LB agar plates (pH 7.3) at 37° C. unless otherwise noted. Antibiotic conditions required for each plasmid construct is listed in Table I.

B. Triparental Mating

Mobilization of plasmid constructs into *P. aeruginosa* 1244 was preformed by a triparental mating system described by Ruvkin and Ausubel (1981). The plasmid to be mobilized contains a ColE1 origin of replication (oriR), an origin of transfer (oriT), as well as the genes to be expressed in the recipient cell, *P. aeruginosa* 1244. The self-transmissible plasmid, pRK2013, will allow the transfer of the mobilizable plasmid into *P. aeruginosa* 1244 when its transfer (tra) genes are expressed. During triparental mating, the self-transmissible plasmid will move into the organism containing the mobilizable plasmid where its Ira genes will be expressed. The tra gene products then cleave the mobilizable plasmid at the oriT and facilitate the transfer of the mobilizable plasmid into the recipient cell. The three bacterial strains, *P. aeruginosa* 1244, *E. coli* HB101 (pRK201 3), and the bacterial strain containing the mobilizable plasmid construct, were incubated over night shaking with the appropriate antibiotic. The optical density of the overnight cultures was measured to ensure equal amounts of cells from each culture were used. The three cultures were mixed together, pelleted, and resuspended in 200 μl of LB broth. A 0.45 μM filter (Millipore, Bedford Mass.) was then placed onto each LB agar plate and incubated overnight. Cells were removed from the filter and resuspended in 5.0 ml of LB broth. Aliquots of this suspension were spread onto agar plates containing the appropriate antibiotics to isolate *P. aeruginosa* 1244 colonies harboring the mobilizable plasmid. Colonies were then tested for the desired phenotype.

C. LPS Extraction

LPS was extracted from bacterial strains using a method described by Hitchcock and Brown (1981). Two ml of cells from an overnight broth culture was pelleted, drained and resuspended with 200 μl of 1×SDS loading buffer (50 mM Tris/HCl pH 6.8, 100 mM DTT, 2% SDS, 0.01% bromophenol blue, 10% glycerol, and 0.001% β-mercapto-ethanol). The sample was heated at 95° C. for 10 minutes, followed by treatment with 25 μg of proteinase K for one hour at 60° C.

D. Bacterial Strains and Plasmids

Table I comprises a list of all bacterial strains and plasmids that were used in this work. A brief description of each bacterial strain and plasmid, including selective media conditions, is included.

E. Preparation of Glycosylated *P. aeruginosa* 1244 Pilin

1. Small-Scale Pilin Extraction

In cases where *P. aeruginosa* was tested for pilin production, a small-scale pilin extraction was performed. For SDS-polyacrylamide gel electrophoresis (PAGE) pilin was prepared from whole cells. Overnight plate cultures were suspended in 5.0 ml LB broth, pelleted, and resuspended in 1.0 ml of 1×SDS-loading buffer. This suspension was heated at 95° C. before analysis. For isoelectric focusing, overnight plate cultures were suspended in 5.0 ml of LB broth and depiliated by vortexing. Cellular debris was removed by centrifugation and the remaining pili in the supernatant was precipitated with 0.5 M NaCl and 3% PEG. The precipitate was removed by centrifugation and resuspended in 1% n-octyl-β-D-glucopyranioside (BOG).

TABLE I

Bacterial Strains and Plasmids Used

| Bacterial Strains | Description | Selective conditions | Reference |
|---|---|---|---|
| *P. aeruginosa* 1244 | Wild type Serogroup O7 strain | None | Castric and Deal, 1989 |
| *P. aeruginosa* 103 | Wild type Serogroup O11 strain | None | Castric, 1995 |
| *P. aeruginosa* 1244N3 | Pilin deficient due to an inactivated rpoN gene | LB $Tc^{50}$ | Ramphal et al., 1991 |
| *P. aeruginosa* 1244Q13 | Pilin deficient due to an inactivated rpoN gene | LB $Km^{400}$ | This work |
| *E. coli* DH5α | Highly transformable strain | None | Gibco, BRL Life Technologies |
| *E. coli* HB101 | Highly transformable Strain | None | Maniatis et al., 1989 |
| Plasmids | | | |
| PDS300 | Contains the O-antigen gene cluster of *E. coli* 0157 | LB $Km^{35}$ | Maurer et al., 1999 |
| PLPS2 | Contains the O-antigen gene cluster of *P. aeruginosa* O11 | LB $Tc^{10}$ | Goldberg et al., 1992 |
| PRK2013 | Self-transmissible plasmid | LB $Km^{35}$ | Ruvkin and Ausubel, 1981 |
| PKT210 | Contains Cm cassette surrounded by PstI sites | LB $Cm^{25}$ | Bagdasarian et al., 1981 |
| PK111 | Contains rpoN::Tet$^r$ surrounded by PstI | LB $Tc^{10}$ | Ramphal et al., 1991 |
| PUC-4K | Contains Km cassette surrounded by PstI | LB $Km^{35}$ | Amersham Pharmacia Biotech |
| PLAFR1 | Broad host range cosmid vector | LB $Tc^{10}$ in *E. coli*; LB $Tc^{50}$ in *P. aeruginosa* | Friedman et al., 1982 |
| PeX18Tc | Allele replacement vector | LB $Tc^{10}$ | Hoang et al., 1998 |
| PEX18Gm | Allele replacement vector | LB $Gm^{10}$ | Hoang et al., 1998 |
| PDIG(1–6) | Contains the O-antigen gene cluster of *E. coli* O157 | LB $Tc^{10}$ in *E. coli*; LB $Tc^{50}$ in *P. aeruginosa* 1244 | This work |
| PAD099 | pEX18Gm without PstI site in the multiple cloning region | LB $Gm^{10}$ | This work |
| PAD100 | rpoN::Tc$^r$ from pKI11 cloned into pEX18Gm | LB $Gm^{10}$ $Tc^{10}$ | This work |
| PAD200 | rpoN::Cm$^r$; Cm from pKT210 | LB $Gm^{10}$ $Cm^{25}$ | This work |
| PAD300 | rpoN::Km$^r$; Km from pUC-4K | LB $Gm^{10}$ $Km^{35}$ | This work |
| PAD400 | rpoN-Km$^r$ from pAD300 cloned into pEX18Tc | LB $Tc^{10}$ $Km^{35}$ | This work |

Km = Kanamycin, Tc = Tetracycline, Cm = Chloramphenicol, Gm = Gentamicin

All antibiotic concentrations in μg/ml for *E. coli* unless otherwise noted

2. Large-Scale Pilin Extraction and Purification

In cases where a large amount of pilin (0.5–0.6 mg) was required for matrix-assisted laser desorption/ionization (MALDI) analysis, the large scale pilin extraction and purification protocol was used (Castric, unpublished protocol). Each precipitation step in this protocol was performed by bringing suspensions to a final concentration of 3.0% polyethylene glycol (PEG) and 0.5 M NaCl or 0.5 M $MgCl_2$. *P. aeruginosa* 1244, harboring the desired plasmid constructs, was streaked to single colonies on selective agar plates from frozen stock cultures and grown overnight. A single colony from the overnight plate was then used to inoculate 10 ml of selective broth medium and incubated overnight shaking at 225 rpm. The overnight culture was then dispersed onto selective agar medium that was poured into 2 Pyrex casserole dishes (240×345×50 mm) and incubated overnight. The following day, cells were harvested, suspended in 300 ml LB broth and depiliated by vortexing. Cellular debris was removed by centrifugation (5000 rpm/15 min./GSA Sorvall rotor) and the remaining supernat ant was precipitated with PEG and $MgCl_2$ for 4–5 hours at 4° C. The precipitate was removed by centrifugation (9000 rpm/30 min./GSA Sorvall rotor), resuspended with 300 ml 10.0 mM Tris/HCl, pH 7.60, containing 20% sucrose, and incubated overnight at 4° C. The following day, the mixture was agitated and the remaining debris was removed by centrifugation (4000 rpm/15 min./GSA Sorvall rotor). The supernatant was precipitated as before, and stored at 4° C. for 2 hours. The precipitate was removed by centrifugation (9000 rpm/30 min./GSA Sorvall rotor), resuspended in 300 ml deionized $H_2O$ and stored at room temperature for 30 min. The precipitate was removed by centrifugation (4000 rpm/15 min./GSA Sorvall rotor) and discarded. To the supernatant, PEG and NaCl were added and stored on ice for 30 minutes. The precipitate was removed by centrifugation (9000 rpm/30.min./GSA Sorvall rotor), resuspended in 150 ml of deionized $H_2O$, and stored. After centrifugation (4000 rpm/15 min/GSA Sorvall rotor), the pellet was discarded and the supernatant was precipitated with PEG and NaCl. The suspension was stored on ice for 30 minutes, pelleted (4000 rpm/30 min./GSA Sorvall rotor) and drained. The pellet was then resuspended with 75 ml deionized $H_2O$, stored at room temperature for 30 minutes, divided evenly between three 50 ml centrifuge tubes and pelleted by centrifugation (5000 rpm/15 min./SS34 Sorvall rotor). The precipitate was discarded and the supernatant was precipitated with PEG and NaCl. The suspensions were stored on ice for 30 minutes, pelleted (9000 rpm/30 min./SS34 rotor), and drained. Each pellet was resuspended with 9.6 ml deionized $H_2O$, stored at room temperature for 30 minutes and transferred to 1.5 ml microcentrifuge tubes in 1.2 ml aliquots. The precipitate was removed by centrifugation and the supernatant was placed into fresh tubes and precipitated once again with PEG and NaCl. The mixture was stored on ice for 15 minutes, pelleted, drained, resuspended with 1.2 ml deionized $H_2O$ and stored at room temperature for 30 minutes. The last precipitation step was then repeated. Pilin was quantitated by the Bio-Rad Protein Assay and analyzed by SDS-PAGE and silver stain for purity (both methods are described below). Pilin isolated from this protocol were stored dry at −20° C., or wet at 4° C.

F. Characterization of LPS and Pilin Proteins

1. Sodium Dodecyl Sulfate Polyacrylamide Gel Electrophoresis (SDS-PAGE)

LPS and pilin extracts were separated by SDS-PAGE according to the standard procedure by Laemmli (1970) using the Novex X-Cell Surelock™ Mini-Cell system. Polyacrylamide gels were cast in 1.0 mm Invitrogen cassettes (Carlsbad, Calif.) at concentrations ranging from 12% T to 17.5% T for the separating gel. Samples were prepared as described earlier. The gels were run in 1× Tris/glycine buffer (25 mM Tris, 250 mM glycine, 0.1% SDS). Kaleidoscope and SDS-PAGE broad range pre-stained standards (Bio-Rad, Hercules, Calif.) were run with each gel. A variation of this procedure was used where only the running buffer was changed from Tris/glycine to Tris/Tricine. In this procedure, the Novex apparatus was run with an inner chamber cathode buffer (0.1 M Tris, 0.1 M Tricine, 0.1% SDS) and an outer chamber anode buffer (0.2 M Tris/HCl pH 8.9).

2. Western Immunoblot Analysis

Western immunoblot analysis was used to visualize serotype-specific reactions with monoclonal and polyclonal antisera between LPS and pilin samples. After completing PAGE separation, LPS and pili were electroblotted on to 0.2–0.45 μm nitrocellulose (NC) paper (Micron Separations Inc. Westborough, Mass.) by using the Bio-Rad Mini Trans-blot® Electrophoretic Transfer Cell at a constant voltage of 100V for 20 minutes in a trans-blot buffer (25 nM Tris, 192 mM glycine, 20% methanol, approximate pH 8.3). Upon completion, the NC paper was removed and blocked for 20 minutes in Killer Filler (KF) (200 ml of 0.1 M NaOH supplemented with 10 g of casein and added to 1.8 L of Phosphate Buffer Saline (PBS) [5.3 L deionized $H_20$, 28 g NaCl, 0.7 g KCl, 4.0 g $Na_2HPO_4$, 0.35 g $CaCl_2$-$2H_20$; 0.54 g $MgCl_2$-$6H_20$] containing 10 g of bovine serum albumin. The pH of the solution was adjusted to 7.4, followed by the addition of 0.2 g of phenol red and 3.6 g of sodium azide [Lynette Young of the Walter Reed Army Institute of Research, personal communication]). When completed, the NC paper was then treated overnight with a primary antibody solution (Table II) that was diluted 1:1000 in KF. The NC paper was then washed 3 times in 10-minute intervals with PBS. After thoroughly washing the NC paper, a phosphatase conjugated secondary goat anti-mouse or goat anti-rabbit (Table II) antibody diluted in KF 1:1000 was added for 90 minutes. Following secondary antibody treatment, the NC paper was washed twice with PBS and once with 50 mM Tris/HCl pH 8.0. Reactions were visualized by adding a developer solution comprised of 10 mg Napthol AS-MX phosphate (Sigma Chemical, St. Louis, Mo.), 20 mg Fast-Red (Sigma Chemical, St. Louis, Mo.) dissolved in 10 ml 50 mM Tris/HCl pH 8.0 while gently shaking. A positive reaction was indicated by the appearance of red bands. Rinsing the NC paper with tap water for several seconds terminated the reaction.

TABLE II

Antisera Used in this Work

| Antiserum | Dilution in KF | Description | Reference or Source |
|---|---|---|---|
| Primary: Monoclonal | | | |
| 6.45 | 1:1000 | Anti-*P. aeruginosa* 1244 pilin | Castric and Deal, 1994 |
| 11.14 | 1:1000 | Anti-*P. aeruginosa* 07 LPS | Sadoff et al., 1985 |
| 16.13 | 1:1000 | Anti-*P. aeruginosa* 011 LPS | ERF Company, Montreal, Canada |
| Polyclonal | | | |
| Anti-*E. coli* O157:H7 | 1:100 | Anti-0157LPS | Becton Dickinson Microbiology Systems, Cockeysville, MD |
| Secondary: | | | |
| Anti-mouse IgA + AgG + IgM(H + L) | 1:1000 | Goat derived | Kirkegaard and Perry Laboratories, Gaithersburg, MD |
| Anti-Rabbit Igg(H + L) | 1:1000 | Goat derived | Kirkegaard and Perry Laboratories, Gaithersburg, MD |

3. Silver Staining of SDS-PAGE Gels

LPS and pili separated on SDS-PAGE gels were also visualized by a silver staining procedure described by Nesterenko (1994). After separation was complete, the SDS-PAGE gel was fixed for 5 minutes in 60.0 ml of 50% acetone that contained 1.5 ml of 50% trichloroacetic acid and 27 μl of 37% formaldehyde. The gel was rinsed in $dH_20$ for 5 minutes, treated for 5 minutes with 60 ml of the 50% acetone, and pretreated with 100 μl of $Na_2S_2O_3.5H_20$ in 60 ml $dH_20$ for 1 minute. After impregnating the gel for 8 minutes in a $AgNO_3$ stock (0.8 ml $AgNO_3$, 0.6 ml 37% formnaldehyde, 60 ml $dH_20$) the gel was rinsed with $dH_20$ and visualized with a developing solution (1.2 g $Na_2CO_2$, 25 μl 37% formaldehyde, 25 μl $Na_2S_2O_3.5H_20$ in 60 ml $dH_20$) for 10–20 seconds. Once the LPS or pilin bands were visible, the reaction was terminated by the addition 1% glacial acetic acid. The gel was then rinsed with destain (40% methanol, 10% acetic acid) and air dried in BioDesign Inc. Gel Wrap and stabilization cassette (Carmel, N.Y.).

4. Isoelectric Focusing Gel Electrophoresis

Isoelectric focusing was used to determine the isoelectric point of pilin proteins. In this work, isoelectric focusing was performed using the LKB-Pharmacia Phastsystem with 0.2% polyacrylamide pre-cast Phastgels™ ○ IEF 3–9 (Amersham Pharmacia Biotech, Uppsala, Sweden) as described by the manufacturers protocol. Prior to protein separation, gels were soaked for 30 minutes in 10 ml of LKB Pharmacia Ampholine® preblended pH 3.5–9.5 for IEF (Uppsala, Sweden) and 2% BOG. Pilin samples were extracted as described previously and suspended in 1% BOG. When separation was complete, proteins were transferred to 0.2 μm PVDF membrane (Bio Rad Laboratories, Hercules Calif.) by diffusion blotting for 2.5 hours. Prior to this step, the PVDF membrane was incubated in 10 ml 50% methanol. The PVDF membrane, containing the adsorbed proteins, was then blocked in KF and treated as described in the Western blot protocol.

5. Colony Immunoblotting

In order to determine if colonies were expressing serotype-specific O-antigen, colony immunoblots were performed. Cells were spread onto agar plates containing the appropriate selective antibiotics and incubated overnight. Osmonics™ Nitrobind nitrocellulose transfer membrane 0.45 μm, 82 mm (Minnetonka, Minn.) was placed directly onto the colonies and carefully lifted off after marking its orientation on the agar plate. Appropriate positive and negative controls were then placed onto the membrane with a sterile toothpick. The membrane was then blocked with KF and treated as described in the Western blot protocol.

6. Slide Agglutination Serum Tests

Slide agglutination serum tests are a simple and rapid method for determining reactivity between surface antigens and serotype-specific antibodies. This test was used to determine if the *E. coli* O157:H7 O-antigen epitope was present on the surface of *P. aeruginosa* 1244. All tests were performed along side a positive [*E. coli* LE392 (pDS300)] and a negative [*P. aeruginosa* 1244] control. *P. aeruginosa* 1244, harboring a plasmid containing the *E. coli* O157:H7 O-antigen gene cluster, was grown to single colonies on selective agar plates. A single colony was suspended in 10 μl of phosphate buffer saline (PBS) and placed on a microscope slide. 5 μl of *E. coli* O157:H7 polyclonal antiserum (Becton Dickinson, Cockeysville, Md.) was added and the suspension was viewed under a dissection microscope following a 2–3 minute incubation. A positive reaction was indicated by clumping of the cells into a granular appearance that was clearly distinguishable from the negative control, *E. coli* HB101.

7. Protein Quantitation

For situations in which it was necessary to quantitate pilin proteins, the Bio-Rad Protein Assay (Hercules, Calif.) was used. This method is based on the assay described by Bradford (1976) and consists of measuring the differential color change of a dye solution in response to various concentrations of proteins using bovine serum albumin (BSA) as a control. Briefly, sample proteins were suspended in 200 μl of the Bio-Rad Protein Assay Dye Reagent Concentrate and brought to a final volume of 1 ml with $dH_20$. The absorbance was then measured with a Unico 2400 UV Spectrophotometer (Dayton, N.J.) at 595 nm. The relative sample protein concentration was then estimated by comparing the absorbance values to those of the control on a standard curve (control $O.D._{595}$ as Y-axis, control protein concentration as X-axis).

8. Matrix-Assisted Lazer Desorption Ionization (MALDI) Mass Spectrometry

When purified pilin was needed for MALDI analysis, proteins were first quantitated, dialyzed against 10 mM ammonium acetate and lyophilized using a Virtis Research Lyophilizer (Gardiner, N.Y.). Dried pilin samples were then analyzed by Dr. Mark Bier at the Mellon Institute Center for Molecular Analysis at Carnegie Mellon University using a PerSeptive Biosystems Voyager STR with DE and a high m/z detector.

G. DNA Techniques

1. Agarose Gel Electrophoresis

The results of plasmid and genomic DNA extractions as well as the results of restriction enzyme digests were analyzed by agarose gel electrophoresis. In addition, this procedure was also performed to purify DNA prior to its use in cloning. The percent of agarose used in this work varied from 0.4% to 0.8% and were cast in either a International Biotechnologies, Inc. (IBI) (New Haven, Conn.) mini-gel apparatus or a IBI medium-gel apparatus. The gels were run at a constant voltage of 100V for the mini-gel apparatus, and from 100–150V for the medium-gel apparatus in 1×TBE buffer (89 mM tris, 89 mM boric acid, 2 mM EDTA, pH 8.3). DNA samples were run along side Roche Molecular Biochemicals molecular weight standards, either a 1 kb DNA ladder or a λ Hind III digest (Mannheim, Germany). After each run, the agarose gel was stained in ethidium bromide (EtBr) (2.5 μg/ml in $dH_20$) for 10 minutes and then subsequently destained in $dH_20$ for an additional 10 minutes. Bands were visualized by placing the gel on a Spectroline Model TR-302 UV transilluminator and photographed with a Fisher Scientific Electrophoresis System Photo-Documentation Camera (Pittsburgh, Pa.).

2. Isolation of Plasmid and Genomic DNA

Plasmid DNA mini-preps and large-scale preps were isolated by a standard alkaline lysis method as described by Maniatis (1982). Genomic DNA was prepared from 1.0 ml of an overnight broth culture, pelleted by centrifugation and resuspended in 400 μl of lysis buffer ( 13.5 mM EDTA, 50 mM NaCl, 10 mM Tris/HCl and 0.5 mg/ml lysozyme, pH 8.0) and incubated 15 minutes at 37° C. To this mixture 2.0 μl of Rnase solution (10 mg/ml) (Sigma Chemical, St. Louis, Mo.) was added and incubated for 15 minutes at 37° C. Once complete, 100 μl or Pronase solution (5 mg/ml) (Sigma Chemical, St. Louis, Mo.) was added and incubated for an additional 15 minutes. The sample was then divided into two microcentrifuge tubes and extracted twice with Tris-saturated phenol and twice with chloroform/isoamyl alcohol (24:1). The genomic DNA was then precipitated with 2 volumes of absolute ethanol, stored at −20° C. for 20 minutes and pelleted by centrifugation. The pellet was rinsed with 70% ethanol, dried in a vacuum dessicator and resuspended with either deionized water for PCR, or TE buffer (10 mM Tris/HCl, pH 7.4, 1 mM EDTA) for restriction digestion.

3. Phenol/Chloroform Extractions

Phenol and chloroform extractions were performed after restriction enzyme digests of plasmid DNA to remove proteins or other contaminants that could interfere with cloning. In this procedure, an equal volume of phenol (neutralized with 1.0 M Tris/HCl, pH 8.0) was added to the DNA solution, followed by vortexing and centrifugation. The upper aqueous phase was removed, placed in a fresh vial, and treated with phenol:chloroform:isoamyl alcohol (25:24:1) followed again by vortexing and centrifugation. Lastly, the aqueous phase was remove and treated only with chloroform:isoamyl alcohol (24:1) to remove all traces of phenol. After centrifugation, the DNA from the aqueous phase was recovered by ethanol precipitation.

4. Ethanol Precipitation of DNA

DNA was recovered from an aqueous solutions by ethanol precipitation. In this procedure, the DNA solution was mixed with 1.0 μl of glycogen (20 μl/ml, Roche Diagnostics GmbH, Mannheim, Germany) 0.25 volume 10 M ammonium acetate, and 2 volumes of absolute ethanol and then stored at −80° C. for 15 minutes. Following incubation, the DNA was pelleted by centrifugation and dried for 15 minutes in a Savant Instruments SC110 speed vacuum. The DNA pellet was then resuspended in 10 mM Tris/HCl, pH 8.5, unless otherwise noted.

5. DNA Quantification

Before ligation of insert DNA to plasmid DNA, both were quantitated to maximize ligation reactions. In this work, DNA was quantitated by agarose gel electrophoresis and UV spectrophotometry. DNA quantitated by agarose gel electrophoresis was performed by running the sample DNA along side varying amounts of λ phage DNA of known concentration. After EtBr staining, the intensity of the sample DNA fragment was compared to that of the λ phage DNA and the approximate concentration was determined. In addition, DNA was quantitated by using the Perkin Elmer MBA 2000 UV spectrophotometer as described by the manufacturer specifications.

6. Establishing Conditions for a Partial Digestion of High Molecular Weight DNA

This procedure was performed using a variation of a standard protocol described by Maniatis (1987) for the preparation of 20 Kb fragments from high molecular weight DNA. A reaction mixture with a final volume of 150 μl containing 1 μg of high molecular weight DNA and EcoR I restriction enzyme buffer was prepared and mixed well. 30 μl of this DNA solution was dispensed into a single microcentrifuge tube, labelled 1, while 15 μl was distributed to 8 microcentrifuge tubes labelled 2–9. All 9 tubes were chilled on ice for 30 minutes. 4 units of restriction enzyme EcoR I was added to tube 1, followed by repeatedly inverting the tube to ensure the contents were mixed well. 15 μl of this reaction was then transferred to tube 2 and mixed as described above. The two-fold serial dilution was repeated through tube 8 while nothing was added to tube 9. All 9 tubes were incubated at 37° C. for one hour, followed by heating at 60° C. for 20 minutes to stop the reaction. The samples were then analyzed by agarose gel electrophoresis through a 0.4% agarose gel that was run overnight at a constant voltage of 10 V. The lane containing DNA fragments in the 20 Kb region was chosen and the amount of enzyme used to obtain this partial digestion was calculated.

7. Construction of pDIG1-6

Figure 2:
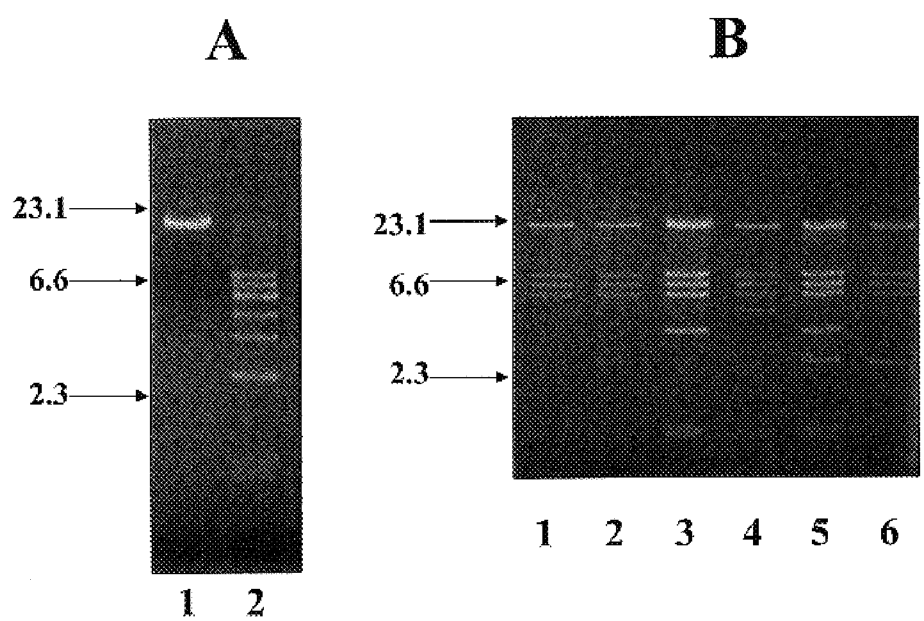
FIG. 2 depicts cloning of the *E. coli* O157:H7 O-antigen gene cluster into the broad-host-range cosmid vector, pLAFR1. Panel A: lane1: pLAFR1 (EcoRI); lane 2: pDS300 (EcoRI); Panel B: lanes 1–6: *E. coli* O157:H7 O-antigen positive pLAFR1 clones (EcoRI). Six positive clones were chosen from the colony immunoblot (FIG. 1) for further analysis. The cosmids were isolated from each clone, treated with EcoRI (Panel B: lanes 1–6), and compared to a total digestion of pLAFR1 and pDS300 (Panel A: lanes 1 and 2, respectively). The cosmids contained similar DNA fragments, thus were then named pDIG1 and pDIG6, respectively. Arrows indicate DNA size markers (Kb).

The *E. coli* O157:H7 O-antigen gene cluster is contained within a 30 Kb segment of pDS300 that was produced from cosmid cloning by Denise Schmidt (Schmidt, 1996; Maurer et al., 1999) and was given as a gift by Dr. John Maurer (the University of Georgia, School of Veterinary Medicine). Because pDS300 is unable to replicate in *P. aeruginosa* 1244, the O157:H7 O-antigen gene cluster was subcloned into the broad-host-range cosmid vector, pLAFR1. This was accomplished by establishing a partial digestion of pDS300 into 25–30 Kb segments using the procedure described above. The 25–30 Kb DNA fragments were isolated by EcoR I digestion and ligated to EcoR I treated pLAFR1. Cloned cosmid vector pLAFR1 was then packaged as bacteriophage lambda particles with the Stratagene Gigapack® XL-11 packaging system and used to infect *E. coli* HB101. Transfectants were selected on LB Tc plates where O157:H7-positive clones were identified by colony immunoblot using O157-specific antiserum (FIG. 1). From these plates, six O157:H7 positive clones were chosen that exhibited a strong reaction with the O157:H7-antiserum and grown in broth cultures. The following day, plasmids were isolated from each clone, treated with EcoR I and separated by agarose gel electrophoresis using an EcoR I total digestion of pDS300 as a control. The results of the agarose gel reveals that all six of the O157:H7 positive clones contain the same size DNA fragments as pDS300 (FIG. 2. panel A and B).

Figure 3:
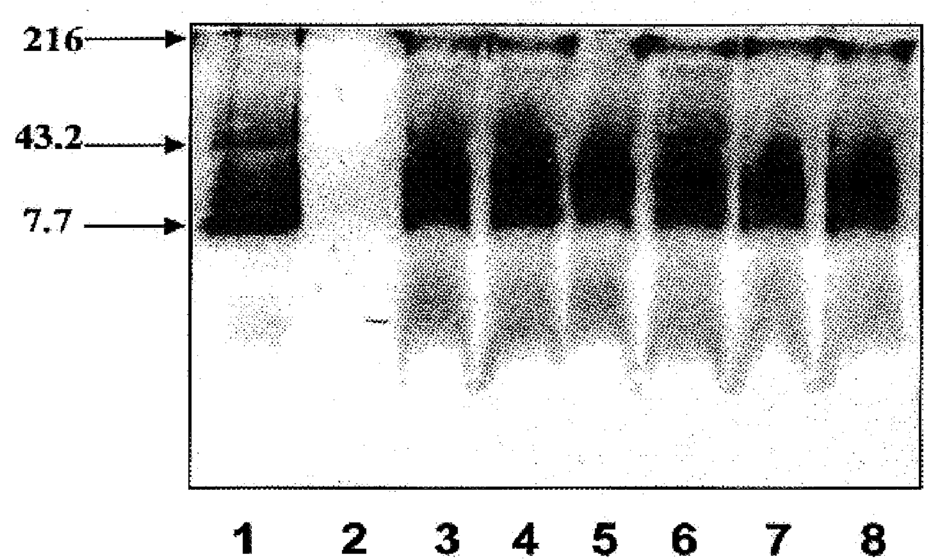
FIG. 3 shows expression of the *E. coli* O157:H7 O-antigen on *E. coli* HB101 LPS. Lane 1: *E. coli* LE392/pDS300; lane 2: *E. coli* HB101; lanes 3–8: *E. coli* HB101/pDIG1 through pDIG6, respectively). LPS was separated on a 17.5% SDS-PAGE gel and electroblotted to nitrocellulose paper. Arrows indicate molecular weight markers (kDa). This blot was analyzed with *E. coli* O157:H7 antiserum.

The next step was to confirm that the LPS of each *E. coli* HB101 clone expressed the O157:1H7 O-antigen. The LPS from each positive clone was then extracted using a method described by Hitchcock and Brown (1983) and analyzed by Western blot using the O157:H7 antiserum. FIG. 3 shows that each of the six *E. coli* HB101 clones reacted with the O157:H7 antiserum, confirming the isolation of the *E. coli* O157:H7 O-antigen gene cluster. The cosmids containing the *E. coli* O157:H7 O-antigen gene clusters were then named pDIG1-6 from their designated lane assignments in FIG. 2, panel B. In total, these results confirm the isolation and cloning of the *E. coli* O157:H7 O-antigen gene cluster into the broad-host-range cosmid vector, pLAFR1, forming pDIG1-6.

8. Preparation of Plasmid and Insert DNA for Cloning

DNA from plasmid preparations were treated with restriction enzymes as recommended by the manufacture specifications to either prepare plasmids for cloning or to remove DNA fragments for cloning into another plasmid. In cases where plasmid DNA contained identical ends, the plasmid was treated with Calf Intestinal Alkaline Phosphatase (CIAP). In situations where it was necessary to remove a restriction site from a multiple cloning region, the plasmid was digested with the enzyme whose recognition site it is to be removed, and then treated with T4 polymerase. Insert DNA was isolated by either polymerase chain reaction (PCR) (described below) or from a plasmid following restriction enzyme digestion. In both cases, the insert DNA was purified by agarose gel electrophoresis and extracted from agarose using the Qiagen Qiaquick Gel Extraction Kit (Valencia, Calif.) according to the manufacture protocol. At this point, both plasmid and insert DNA was ready for ligation.

9. Ligation of Plasmid and Insert DNA; Transfer Into *E. coli*

After the plasmid and insert DNA were prepared and quantitated, they were ligated with a plasmid DNA:insert DNA ratio of 100:200 ng using T4 DNA ligase. Following the ligation reaction, DNA was moved into *E. coli* by either transformation or transfection. For transformation reactions, cloned plasmid DNA was moved into *E. coli* DH5α Competant Cells (Gibco BRL, Life Technologies, Carlsbad, Calif.). In addition, cloned cosmid DNA was packaged as bacteriophage λ particles with the Stratagene Gigapack® III XL Packaging Extract (Stratagene, La Jolla, Calif.) and used to transduce *E. coli* HB101. Both transformation and transfection reactions were performed as described by the manufacturer specifications.

10. Allele Replacement Strategy for *P. aeruginosa*

Allele replacement was performed in *P. aeruginosa* 1244 by a strategy described by Schweizer (1992). For this procedure, plasmids were developed that contained a ColE1 type oriR, a multiple cloning site, an oriT, a counter-selectable sacB genes and an antibiotic resistance marker that allowed for the selection of the plasmid in *E. coli*. A unique feature of these plasmids is the sacB gene that, when expressed in a Gram-negative bacterium, renders the organism sensitive to sucrose. In the procedure, a copy of the allele to be replaced is cloned into the allele replacement plasmid and insertionally mutated by a selectable antibiotic resistance marker. Once the gene is cloned and mutated, the plasmid is transferred from *E. coli* to *P. aeruginosa* by triparental mating. Since this cloned plasmid cannot replicate in *P. aernginosa* due to the ColE1 oriR, one of two events must occur for *P. aeruginosa* to acquire resistance to the marker used to mutate the desired allele. First, the plasmid may integrate into the chromosome by a single homologous recombination event, forming a merodiploid. Second, a double cross-over event can occur, resulting in the loss of the wild type allele and acquistion of the mutated allele. Using this allele replacement strategy, the isolation of the second event is increased by selecting for the double crossover event on sucrose-containing medium.

11. Construction of rpoN Allele Replacement Plasmids

Figure 4:
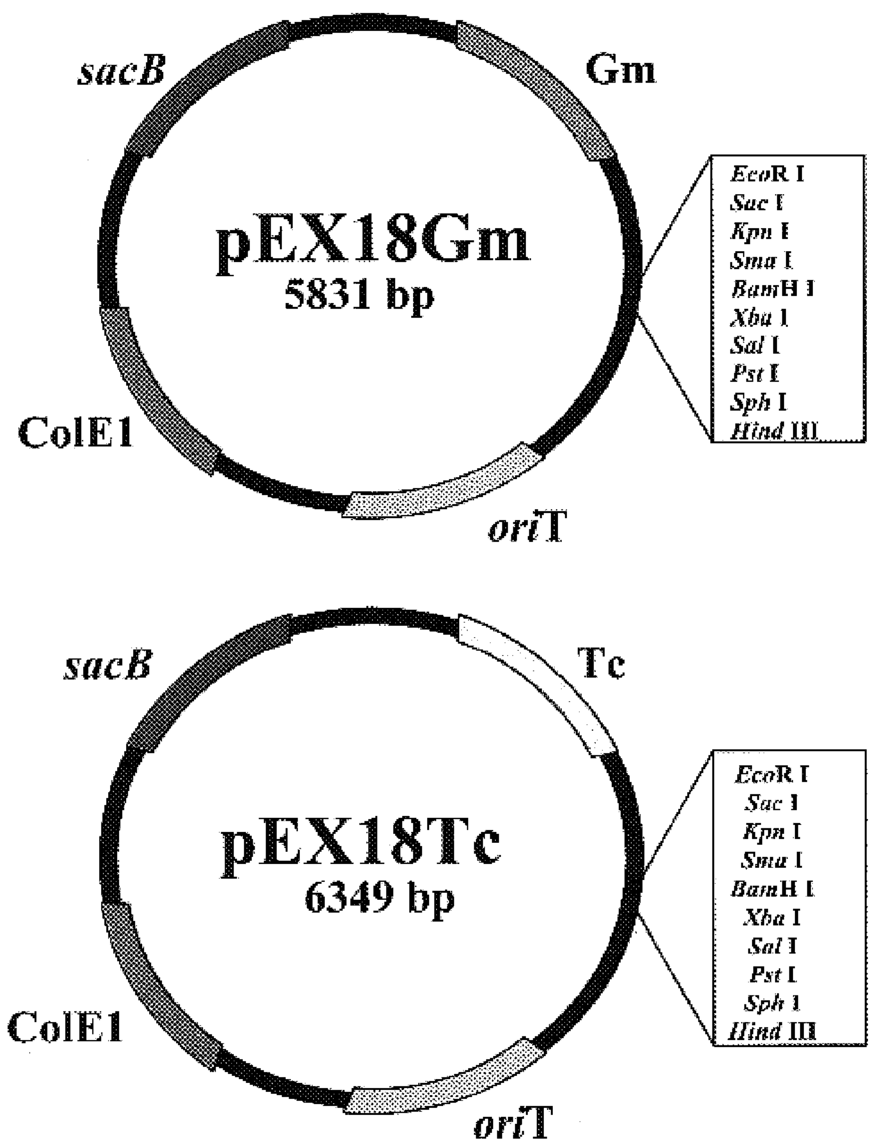
FIG. 4 shows allele replacement plasmids developed specifically for allele replacement in *P. aeruginosa* by Schweizer (1992) and Hoang et al. (1998). They contain a ColE1-type origin of replication (oriR), therefore cannot replicate in *P. aeruginosa*; a multiple cloning region; and origin of transfer (oriT); a counter-selectable sacB gene; and an antibiotic resistance marker that allows for the selection of the plasmids in *E. coli*. A unique feature to these plasmids is the sacB gene that, when expressed in a Gram-negative bacterium, renders the organism sensitive to sucrose.

The allele replacement technique developed by Schweizer (1992) utilizes specially constructed plasmids for use in *P. aeruginosa*. In order to successfully use this technique for the isolation of the rpoN mutant strain of *P. aeruginosa* 1244, the rpoN gene had to be cloned into one of the allele replacement plasmids depicted in FIG. 4. Once cloned, the gene will be mutated by the insertion of a selectable antibiotic resistance marker that will be placed into a unique restriction site within the gene. The rpoN gene is approximately 1.5 Kb and contains a single Pst I recognition site. Insertion of an antibiotic resistance cassette into the Pst I site will leave approximately 0.9 and 0.6 Kb, respectively, of wild type DNA sequences on either side of the marker to sufficiently allow for allele replacement by homologous recombination. In addition, the multiple cloning sites of both allele replacement vectors also contain a Pst I restriction site, but located between EcoR I and Hind III restriction sites (FIG. 4). Hence, treatment of either vector with EcoR I and Hind III will result in the loss of the Pst I recognition site. Initially, the approach was to amplify the rpoN gene from the *P. aeruginosa* 1244 genome. In this procedure, PCR primers were developed that incorporated an EcoR I and Hind III restriction site 5' and 3', respectively, to the rpoN gene. After purification by agarose gel electrophoresis and enzyme treatment, the introduced Hind III restriction site was shown to be nonfunctional by a series of ligation reactions in which the PCR product failed to ligate to itself (data not shown). To correct this problem, two additional primers were developed that contained an introduced Hind III restriction site, but the results were the same for both of the new primers.

Figure 5:
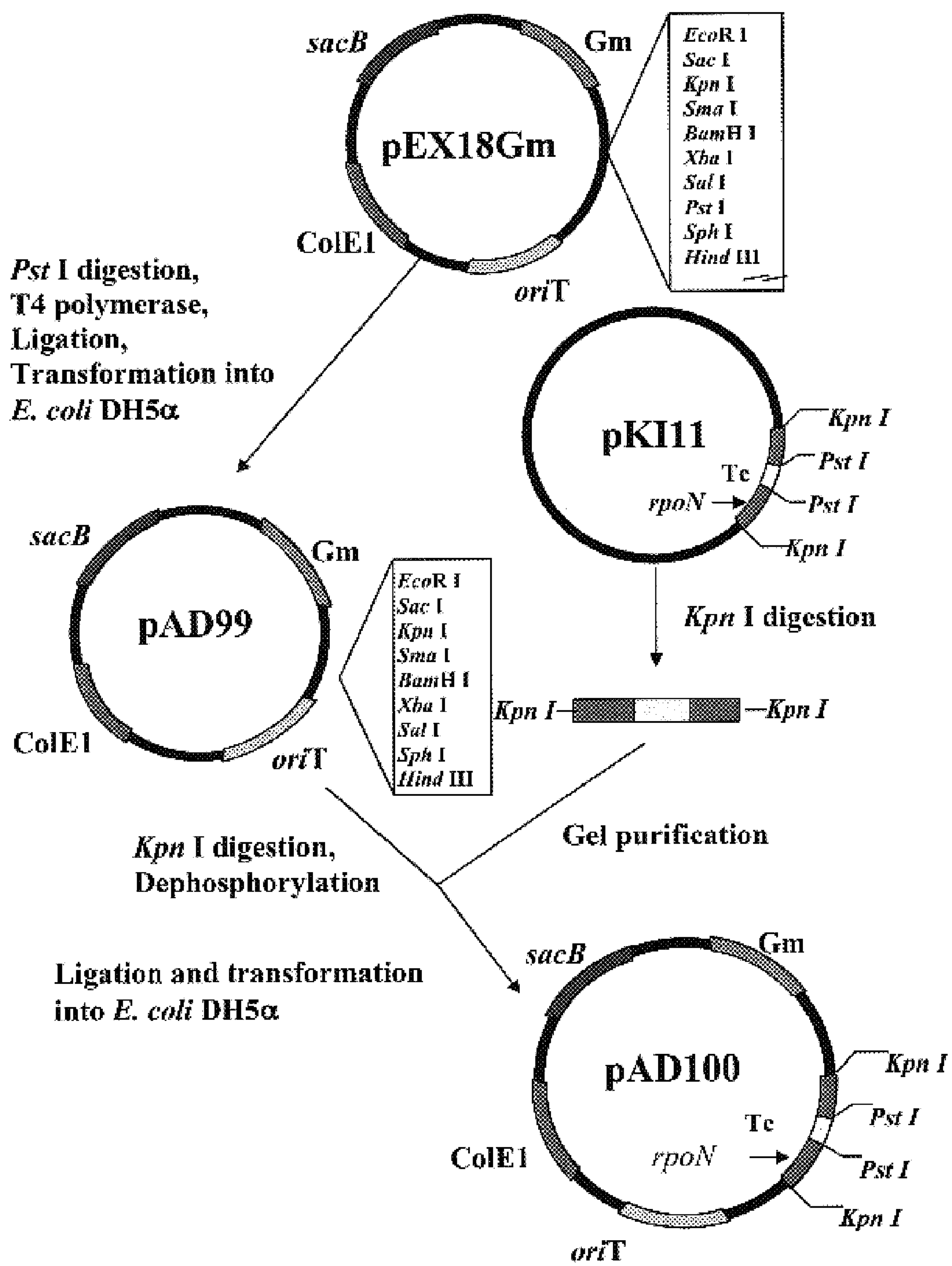
FIG. 5 shows the construction of the rpoN allele replacement plasmid, pAD100. The Pst I recognition site in the multiple cloning region of pEX18Gm was removed using T4 polymerase, forming pA:D99. The rpoN::Tc$^r$ cassette was then removed from pKI11 by Kpn I digestion and cloned into similarly treated pAD99, forming pAD100.
Figure 6:
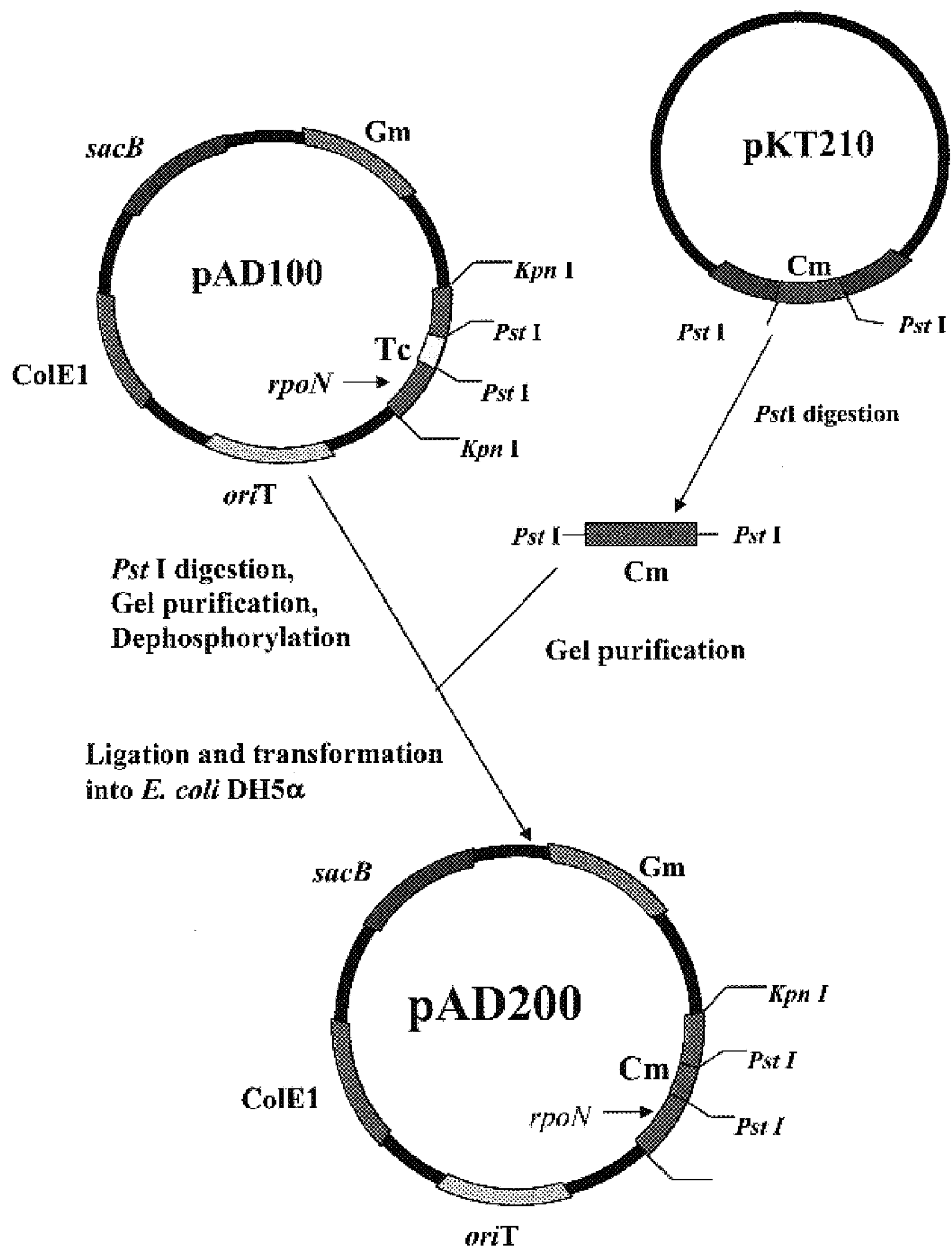
FIG. 6 shows the construction of the rpoN allele replacement plasmid, pAD200. pAD200 was constructed by replacing the Tc$^r$ cassette with a chloramphenicol (Cm$^r$) cassette. The Tc$^r$ cassette was removed from pAD100 by Pst I digestion and replaced with the Cm$^r$ cassette that was derived from pKT210 after similar enzyme treatment.

The rpoN gene is also contained within Kpn I restriction sites in pKI11 (Ishimoto and Lory, 1989). This plasmid was used to isolate strain 1244N3 and contains a $Tc^r$ cassette within the Pst I restriction site of the rpoN gene. As an alternative approach, this mutated gene was isolated by Kpn I digestion, and cloned into one of the allele replacement plasmids. The Tc cassette was replaced with another marker. First, in order to replace the $Tc^r$ cassette within the rpoN gene, the Pst I site had to be removed from the multiple cloning region of pEX18Gm. This was preformed using T4 polymerase on Pst I treated pEX18Gm, followed by an overnight ligation reaction. The DNA from this ligation reaction was then used to transform *E. coli* DH5α cells, followed by selection of the plasmid Gm resistance marker on agar plates. A total of thirty Gm resistant colonies were isolated, six of which underwent further analysis. All six colonies were inoculated in broth culture followed by a plasmid extraction and digestion with Pst I. Two of the six plasmids were found unable to be digested with Pst I, thus forming pAD99 (FIG. 5). Once this plasmid was isolated, the rpoN::$Tc^r$ cassette was removed from pKI11 by Kpn I digestion, purified by agarose gel electrophoresis and ligated to similarly treated pAD99, which had been dephosphorylated with Calf Intestinal Alkaline Phosphatase (CIAP). Following ligation, the DNA was transformed into *E. coli* DH5α and selected on agar plates containing Gm and Tc. Three Gm and Tc resistant colonies were isolated and tested by enzyme digestion, (Pst I, Kpn I, and EcoR I) and PCR using rpoN specific primers to confirm plasmid construction (results not shown). After confirmation, the resulting plasmid was named pAD100 (FIG. 5).

pAD200 and pAD300 (FIGS. 6 & 7, respectively) were then constructed from the newly generated pAD100. pAD200 was formed by replacing the $Tc^r$ cassette with the chloramphenicol ($Cm^r$) gene derived from pKT210 (FIG. 6).

Figure 7:
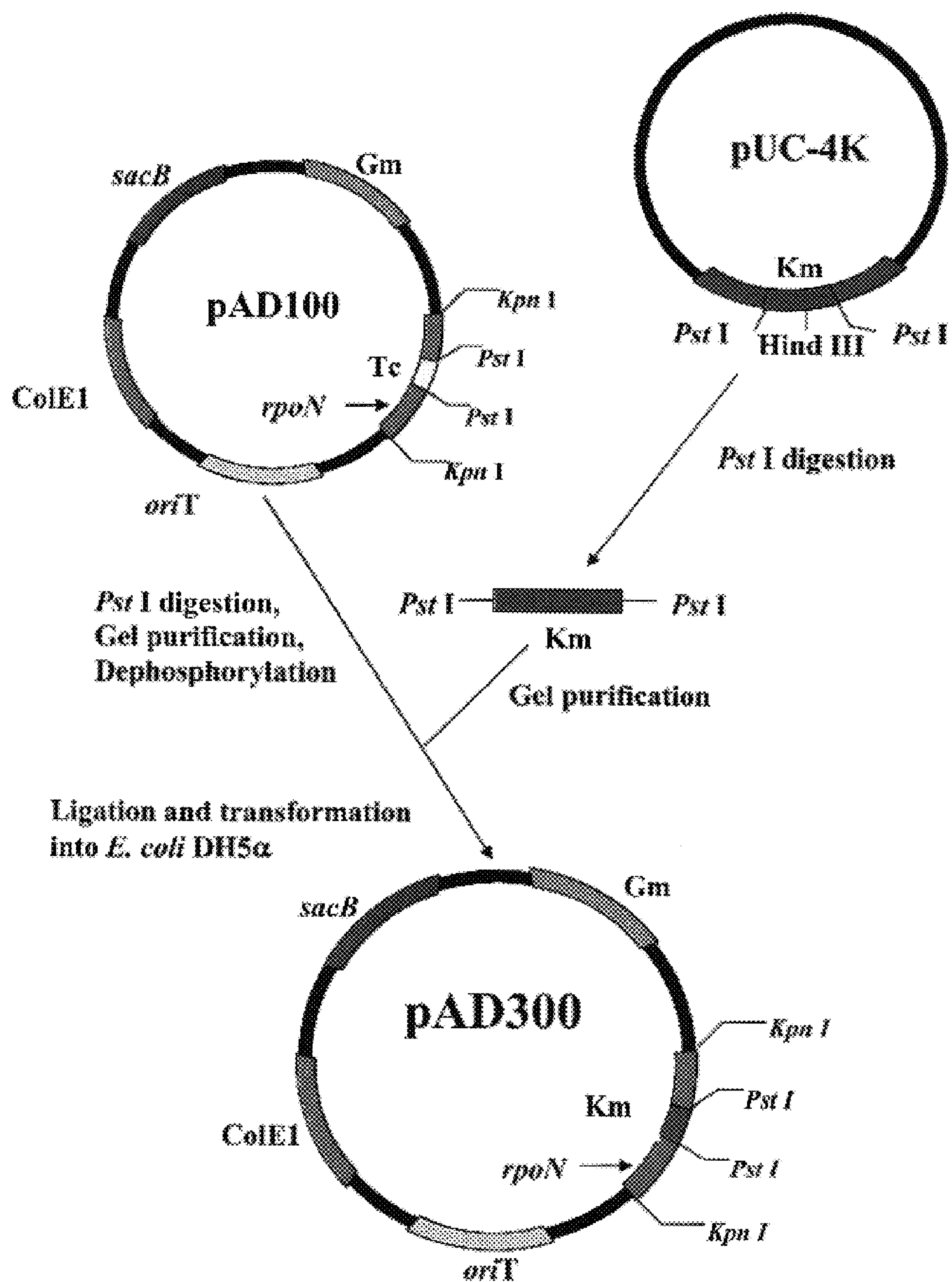
FIG. 7 shows a construction of the rpoN allele replacement plasmid, pAD300. pAD300 was constructed by replacing the Tc$^r$ cassette of pAD100 with a Kanamycin (Km$^r$). The Tc$^r$ cassette was removed from the pAD100 by Pst I digestion and replaced with the Km$^r$ cassette that was derived from pUC-4K after similar enzyme treatment.
Figure 8:
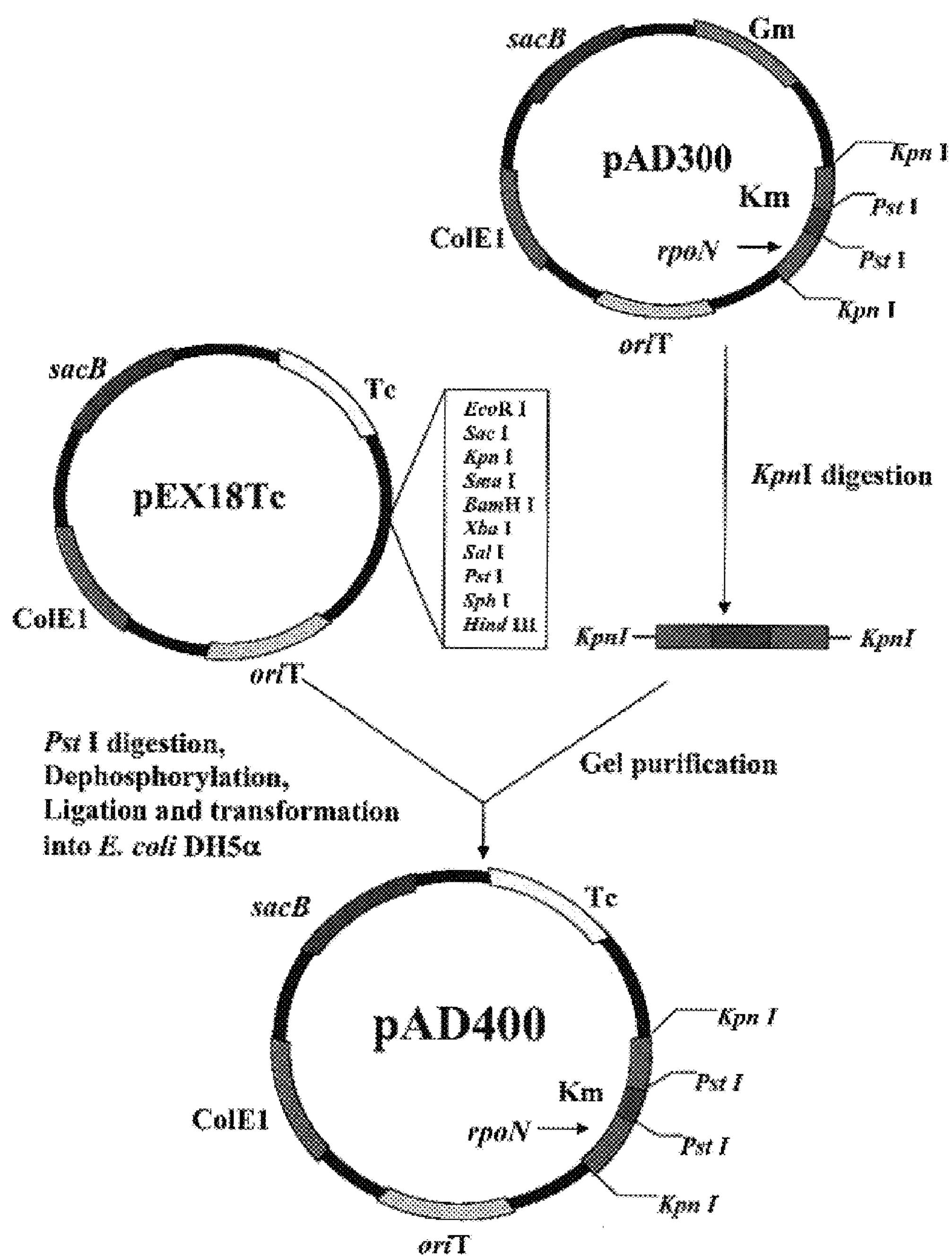
FIG. 8 shows a construction of the rpoN allele replacement plasmid, pAD400. To construct pAD400, the rpoN::Km$^r$ cassette was removed from pAD300 by Kpn I digestion and cloned into similarly treated pEX18Tc.

The construction of pAD300 was performed by replacing the $Tc^r$ cassette of pAD100 with a kanamycin ($Km^r$) cassette that was derived from pUC-4K (FIG. 7). To increase the versatility of the rpoN allele replacement strategy, the rpoN::$Km^r$ cassette was removed from pAD300 by Kpn I digestion and cloned into pEX18Tc, forming pAD400 (FIG. 8). The construction of pAD200 through pAD400 was confirmed as performed for pAD100.

12. DNA Amplification

DNA amplification was performed by using the polymerase chain reaction (PCR) with primers (Gibco BRL, Life Technologies, Carlsbad, Calif.) that were developed from known DNA sequences. Table III lists primers that were used in this work. DNA was amplified from both genomic and plasmid DNA using the Perkin Elmer Cetus DNA Thermal Cycler or the Perkin Elmer GeneAmp® PCR 2400 system. DNA target sequences that ranged from 1.5 to 4 Kb were amplified using the Perkin Elmer GeneAmpg Core Reagent Kit (Perkin Elmer Branchburg, N.J.). Each reaction was performed in a volume of 50 μl and consisted or 200 μM of each dNTP, 1.25 Units of Taq polymerase, 1 μM of forward and reverse primers, 2.5 mM $MgCl_2$, 1×PCR Buffer II, and 1 ng of template DNA. The PCR step cycles were performed as follows: initial step at 97° C. for 1 minute, 25 cycles of (95° C. for 1 minute, 52° C. for 1 minute, 72° C. for 1 minute) and a final step at 72° C. for 10 minutes.

DNA amplification was also attempted for target DNA that ranged from 13 to 17 Kb. For this reaction, long range PCR using the Perkin Elmer GeneAmp® XL PCR kit was employed. The method involved a Hot Start technique that utilized the Perkin Elmer AmpliWax® P-GEM System. The total volume of the lower reagent was 40 μl and consisted of 1×3.3×XL PCR Buffer II, 200 μM of each dNTP, 0.1 –0.5 μM of the forward and reverse primers, and 1 mM of $Mg(OAc)_2$. To this mixture, an AmpliWax® bead was added and heated for 5 minutes at 80° C. The mixture was allowed to cool until a solid wax layer formed over the lower reagent. The total volume of the upper reagent was 60 μl and consisted of 1×3.3×XL PCR Buffer II, 4 Units of rTth DNA Polymerase XL and 1 ng of genomic DNA template. The upper reagent was added directly to the top pf the wax layer and the PCR step cycles were performed as follows: initial step at 94° C. for 1 minute, 25 cycles of (94° C. for 15 seconds, 60° C. for 12 minutes) and a final step at 72° C. for 20 minutes.

TABLE III

Primer Sequences Developed for this Work (SEQ ID NOS 1–8)

| Primer | Sequence (5' → 3') | Description |
|---|---|---|
| NILIP25 | GCC GTC GTG AAT TCG GTA CCA GCG AAT AAG GTA CTA AGC C | RpoN forward |
| NILIP26 | GCT ACG CCT TCG AAC TTG CTG CCG TTC GAG ATA CTT CTC | RpoN reverse |
| NILIP29 | GTT CGT GCC GCA CTT CAA GCC GGG C | HimD forward |
| NILIP30 | TCA GGG TTC TCG CCG CCT CTG GCG A | WbpM reverse |
| NILIP31 | GCT GCC TTC GAC CAA GAA GCG GTT G | Gm reverse |
| NILIP32 | GGA GTA GGT GGC TAC GTC TCC GAA C | Gm forward |
| NILIP33 | GCC GAA GAT AAC GTA GCT GTT CGA AGG GCG GTC GAA CGA AGG GCT G | RpoN reverse |
| NILIP34 | GTC AGC CGA GGC TAC GCC TTC GAA CTT GCT GCC GTT CGA GAT ACT TCT C | RpoN reverse |

H. Southern Blot Analysis

1. Preparation of Probe DNA

The wild type rpoN gene was chosen as the probe for Southern blot analysis in this work and was prepared by nick translation using the BioNick™ Labeling System (Gibco, BRL Life Technologies, Carlsbad, Calif.) as described by the manufacturer protocol. The rpoN gene was isolated by PCR amplification from the *P. aeruginosa* 1244 genome, purified and quantitated by agarose gel electrophoresis, and extracted from agarose as described previously before nick translation. Approximately 1 μg of probe DNA was prepared.

2. Preparation of Genomic DNA and Blotting to Nitrocellulose

Genomic DNA from both wild type *P. aeruginosa* 1244 and the putative mutant strain *P. aeruginosa* 1244Q13 was isolated as described previously. 20 μg of each genomic DNA was digested for 16 hours with BamH I and Hind III and then separated on a 0.8% agarose gel the next day. Following separation, the gel was soaked in 300 ml Gel Soak I (1.5 M NaCl, 0.5 M NaOH) for 20 minutes at room temperature with gentle agitation. The step was repeated once. Next, the gel was soaked in 300 ml Gel Soak II (1 M $NH_3OAc$, 0.05 M NaOH) for an additional 20 minutes at room temperature with gentle agitation. This step was also repeated once. A capillary blot apparatus was then assembled as described by Maniatis (1982) to transfer the DNA from the agarose gel to 0.45 μM NC paper (Micron Separations Inc. Westborough, Mass.). The blotting procedure was carried out for 24 hours. The following day, the NC paper was removed from the gel surface and soaked for 5 minutes in 50 ml 6×SSC medium (20×SSC: 3 M NaCl, 0.3 M $Na_3$ Citrate, pH 7.0). The NC paper was removed from the 6×SSC medium, placed between 2 sheets of 3 MM Whatman paper and dried at room temperature for 10 minutes. The NC paper was then baked for 2 hours at 80° C. in a vacuum oven. At this stage, the NC paper is ready for the pre-hybridization and hybridization step.

3. Pre-hybridization and Hybridization of DNA Probe to NC Paper

After baking, the NC paper was cooled for 10 minutes on the lab bench, hydrated with 50 ml of 2×SSC, and placed in a sealable plastic bag. 5.0 ml of pre-hybridization solution (50% formamide, 5×SSC, 5×Denhardt's solution [50×Denhardt's solution: 1% (w/v) Ficoll, 1% (w/v) polyvinylpyrrolidone, 1% (w/v) BSA], 0.025 M $NaPO_3$ pH 6.5, 0.5 mg/ml salmon sperm DNA) was heated for 10 minutes at 95° C., cooled to room temperature and added to the NC paper. The bag was sealed, mixed well, and incubated for 2 hours at 42° C. Just before incubation was complete, 5.0 ml of the probe/hybridization solution (45% formamide, 5×SSC, 1×Denhardt's solution, 0.020 M $NaPO_3$, pH 6.5, 0.5% Dextran Sulfate, 0.2 mg/ml salmon sperm DNA, 200 ng/ml of probe DNA) was heated for 10 minutes at 95° C. and cooled to room temperature. The prehybridization solution was drained, replaced with the probe/hybridization solution, and incubated overnight at 42° C.

4. Post-hybridization Wash

The following day, the NC paper was removed from the probe/hybridization solution and blot dried with paper towels. The NC paper was washed twice for 15 minutes with 250 ml posthybridization solution 1 (2×SSC, 0.1% SDS), twice for 15 minutes with 250 ml post-hybridization solution 2 (0.2×SSC, 0.1% SDS), twice for 15 minutes with post-hybridization solution 3 (0.16×SSC, 0.1% SDS) and rinsed with 2×SSC for 3 minutes at room temperature.

5. Detection

The NC paper was then washed for 1 minute in 25 ml Buffer I (0.1 M Tris/HCl, 0.15 M NaCl, pH 7.5) and placed in a new plastic bag containing 10 ml of Buffer I supplemented with 0.3 g BSA. The bag was incubated for 1 hour at 65° C. The NC paper was developed using the BluGENE® Nonradioactive Nucleic Acid Detection System as described by the manufacturer specifications. Briefly, the solution was removed from the bag and replaced with 7.0 ml of strepavidin-alkaline phosphatase conjugate (7.0 ml Buffer I, strepavidin-alkaline phosphatase), mixed well, and incubated at room temperature for 10 minutes. The NC paper was then removed, blot dried with paper towels, and washed 3× with 280 ml Buffer I for 15 minutes followed by a 10 minute wash with Buffer II (0.1 M Tris/HCl, 0.1 M NaCl, 0.05 M $MgCl_2$, pH 9.5). The NC paper was then placed in a fresh plastic bag to which 7.5 ml of fresh visualization solution (2.5 mg Nitro Blue Tetrazolium, 12.5 mg 5-bromo-4-chloro-3indolylphosphate, 7.5 ml Buffer II) was added and incubated in the dark for 5–30 minutes at room temperature. The reaction was terminated when bands reached their desired intensity by rinsing the blot with tap water.

Example 1

Cloned Serotype O11 O-antigen Gene Cluster from *P. aeruginosa* PA103 Acts as O-Antigen Source in *P. aeruginosa* 1244 LPS In order to identify whether the O-antigen biosynthetic pathway serves as the source for the pilin glycan, a gene cluster encoding the O-antigen polysaccharides from serotype O11 of *P. aeruginosa* was moved into *P. aeruginosa* 1244 and tested for serotype-specific O-antigen expression on the LPS of this organism. The *P. aeruginosa* O11 O-antigen was chosen for the initial experiment because these genes have been isolated and characterized (Goldberg et al., 1992) and the O-antigen sugar residues are structurally very different from those found on the LPS of *P. aeruginosa* 1244. The *P. aeruginosa* O11 gene cluster is contained within a 15 Kb fragment on pLPS2 and was a gift from Dr. Joanna Goldberg (University of Virginia Health Sciences Center). This plasmid was conjugally transferred into *P. aeruginosa* 1244 by a triparental mating system described by Ruvkin and Ausubel (1981 ) and screened by selecting for the plasmid tetracycline resistance marker (Tc). Two colonies from this mating were chosen for further analysis.

Figure 9:
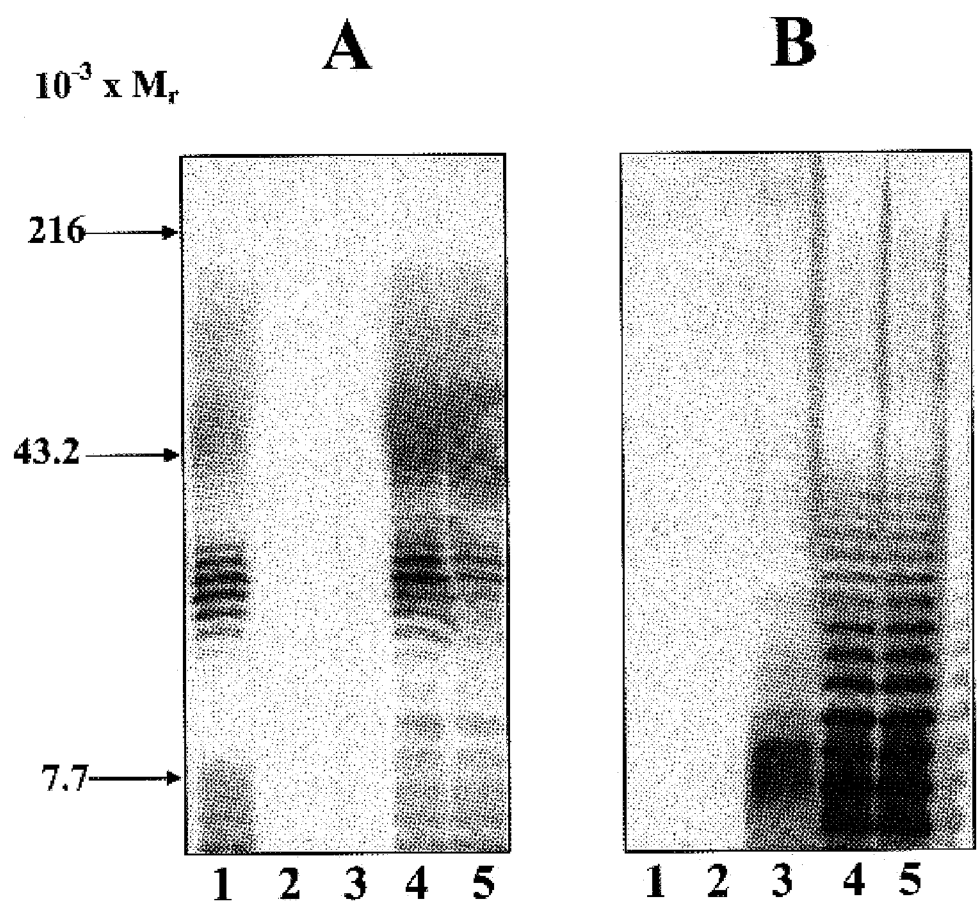
FIG. 9 is a western blot analysis of LPS derived from *P. aeruginosa* 1244/pLPS2. Panel A: Lane 1: *P. aeruginosa* 1244; lane 2: *E. coli* HB101; lane 3: *E. coli* HB101/pLPS2; lanes 4 and 5: *P. aeruginosa* 1244/pLPS2; Panel B: Lane 1: *P. aeruginosa* 1244; lane 2: *E. coli* HB101; lane 3: *E. coli* HB101/pLPS2; lanes 4 and 5: *P. aeruginosa* 1244/pLPS2; LPS was separated on a 12.5% SDS-PAGE gel and electroblotted to 0.2 μm nitrocellulose paper. Arrows indicate molecular weight markers (kDa). Panel A: Analyzed with mAb 11.14, an antiserum specific for *P. aeruginosa* 1244 LPS; Panel B: Analyzed with an anti-PA 011 LPS mAb, 16.13.
Figure 10:
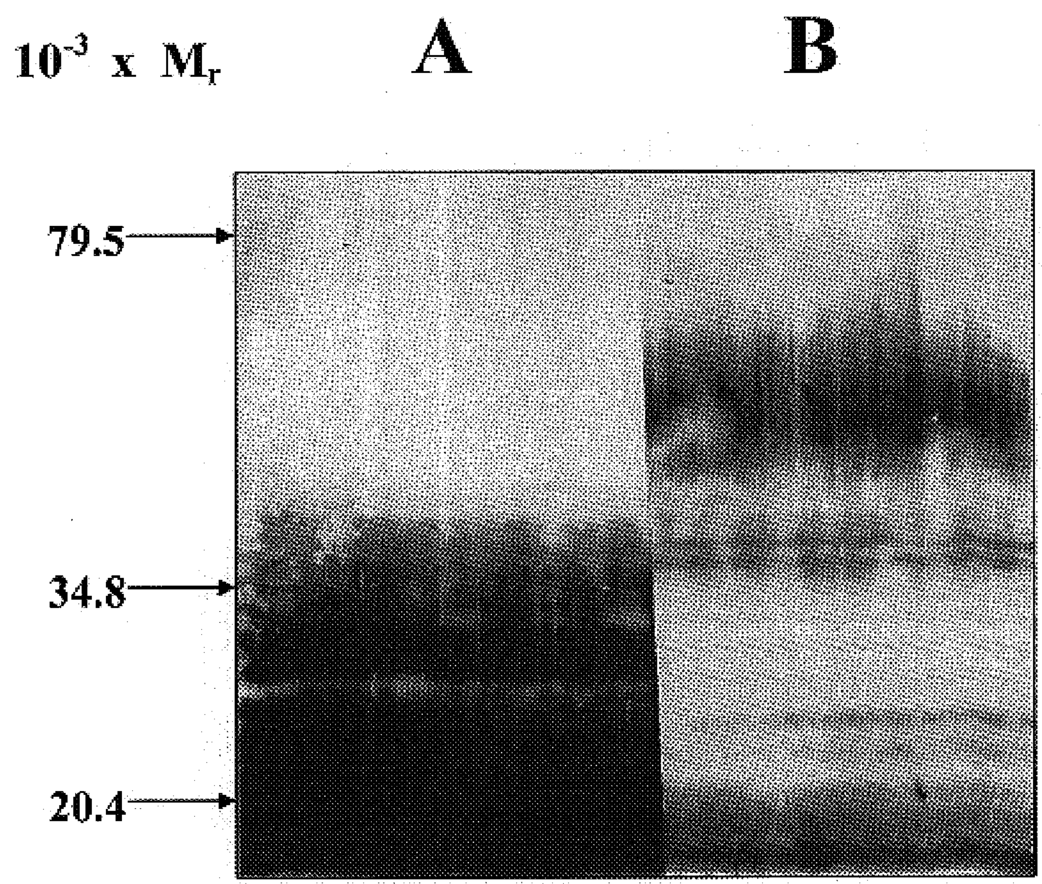
FIG. 10 is a western blot of separate LPS chains derived from *P. aeruginosa* 1244/pLPS2. LPS was separated in one lane on a 12.5% polyacrylamide gel and electroblotted to 0.2 μm nitrocellulose paper. Arrows indicate molecular weight markers (kDa). Panel A: analyzed with anti-011 mAb 16.13; Panel B: analyzed with 1244 anti-LPS mAb 11.14.

First, a plasmid extraction on each Tc resistant colony was performed to ensure plasmid incorporation into *P. aeruginosa* 1244 (results not shown). Then, the LPS from each 1244 strain harboring the pLPS2 plasmid was extracted from overnight broth cultures using the method described by Hitchcock and Brown (1981) and analyzed by Western blot using anti-1244 LPS monoclonal antibody (mAb), 11.14, (FIG. 9, panel A) and an anti-O11 LPS mAb, 16.13 (FIG. 9, panel B). As seen in panel A, lanes 4–5, *P. aeruginosa* 1244/pLPS2 produces the characteristic O-antigen ladder that is observed in the wild type 1244 strain (panel A, lane 1). There was no reaction seen in lanes 2 and 3 containing *E. coli* HB101 and *E. coli* HB101/pLPS2, respectively. In panel B, only the *P. aeruginosa* 1244 and *E. coil* HB101 strains containing pLPS2 (panel B, lanes 3–5) was capable of reacting with 16.13. These results indicate that the LPS of *P. aeruginosa* 1244/pLPS2 contain both the wild type and the serotype O11 O-antigen. To examine if strain 1244 and serotype O11 O-antigen were expressed on separate LPS chains in *P. aeruginosa* 1244/pLPS2, the LPS of this organism was analyzed by Western blot using a preparative gel comb. One half of this blot was reacted with mAb 11.14, while the other half was reacted with mAb 16.13 antiserum. As seen in FIG. 10, the detected pattern of the O-antigen ladder is quite different when reacted with each antiserum. This indicates that *P. aeruginosa* 1244 is producing separate LPS molecules containing either strain 1244 O-antigen or serotype O11 O-antigen.

Example 2

Cloned Serotype O11 Gene Cluster from *P. aeruginosa* PA103 Acts as Pilin Glycan Source in *P. aeruginosa* 1244

Figure 11:
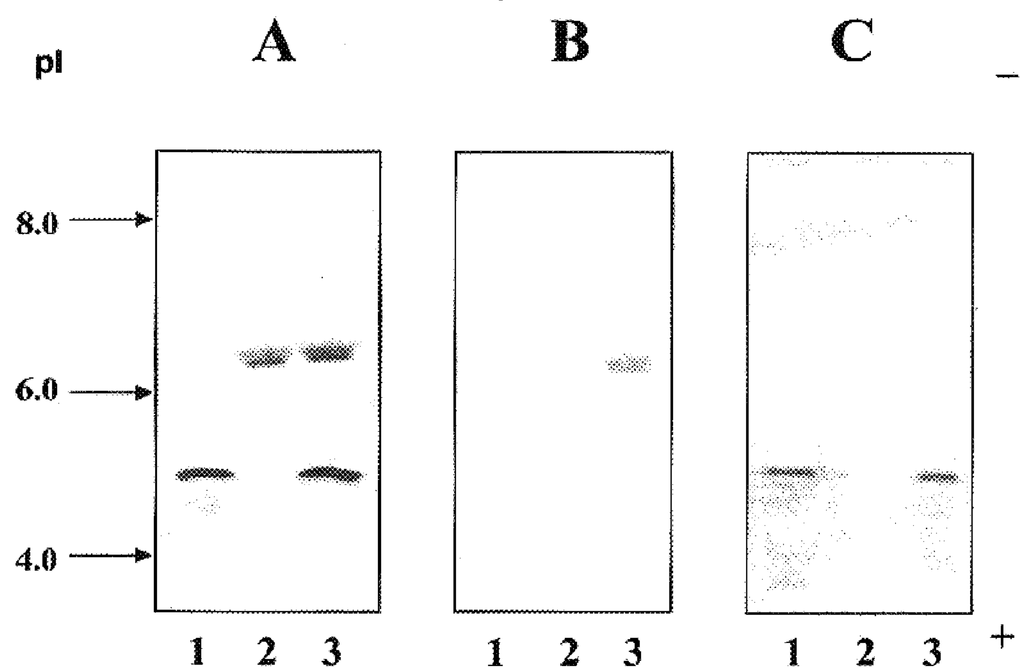
FIG. 11 shows results of isoelectric focusing of *P. aeruginosa* 1244/pLPS2 pili expressing the *P. aeruginosa* PA103 O-antigen. Panels A, B, and C: lane1: *P. aeruginosa* 1244 glycosolated pilin; lane 2: *P. aeruginosa* 1244 non-glycosylated pilin; lane 3: *P. aeruginosa* 1244/pLPS2. Isoelectric focusing was performed using the LKB-Pharmacia Phastsystem as described by the manufacture specifications. Pilin was transferred to PVDF membrane by diffusion blotting. The pI values were determined by focusing standards on the same gel as the samples. Panel A: analyzed with 1244 anti-pilin mAb 6.45, Panel B: analyzed with mAb 16.13; Panel C: analyzed with mAb 11.14.

Once O11 O-antigen expression was established on the LPS of *P. aeruginosa* 1244/pLPS2, the pill of this organism were tested for the presence of the O11 O-polysaccharides. Since the LPS O-antigen ladder will mask pilin analysis, proteins were separated electrophoretically by isoelectric focusing. LPS is a highly negatively charged structure and therefore migrate off of a focusing gel. Pilin proteins separated in this manner successfully removes the LPS. Pilin from *P. aeruginosa* 1244/pLPS2 was extracted from overnight plate cultures and suspended in 1% n-octyl-β-D-glucopyranoside (BOG). BOG is a nonionic detergent intended for solublizing membrane bound proteins in their native state, hence was used in this procedure. Pilin was separated by isoelectric focusing in a pH gradient of 3.0–9.0, transferred to PVDF membrane by diffusion blotting, and reacted with strain 1244 anti-pilin mAb 6.45 (FIG. 11, panel A), anti-O11 LPS mAb 16.13 (FIG. 11, panel B), and strain 1244 anti-LPS mAb, 11.14 (FIG. 11, panel C). The results of the focusing gel using mAb 6.45 reveal that *P. aeruginosa* 1244/pLPS2 is generating two distinct types of pilin, an acidic and a neutral form (panel A, Lane 3). The acidic pilin from the recombinant organism focused to a pI of approximately 4.75, a charge consistent to that exhibited by wild type *P. aeruginosa* 1244 pilin (panel A, lane 1). The neutral pilin from *P. aeruginosa*/pLPS2 focused to a pI of 6.25, a value identical to that exhibited by non-glycosylated *P. aeruginosa* 1244 pilin (panel A, Lane 2). When focusing was performed using mAb 16.13, a reaction was only seen at pI 6.25 (panel B; Lane 3), the same isoelectric point of the neutral pilin observed in panel A. When pilin was focused and analyzed with mAb 11.14, a reaction was only seen with pilin at a pI of 4.75 (panel C; lanes 1 and 3), a charge also exhibited by the pilin of wild type strain 1244.

Figure 18:
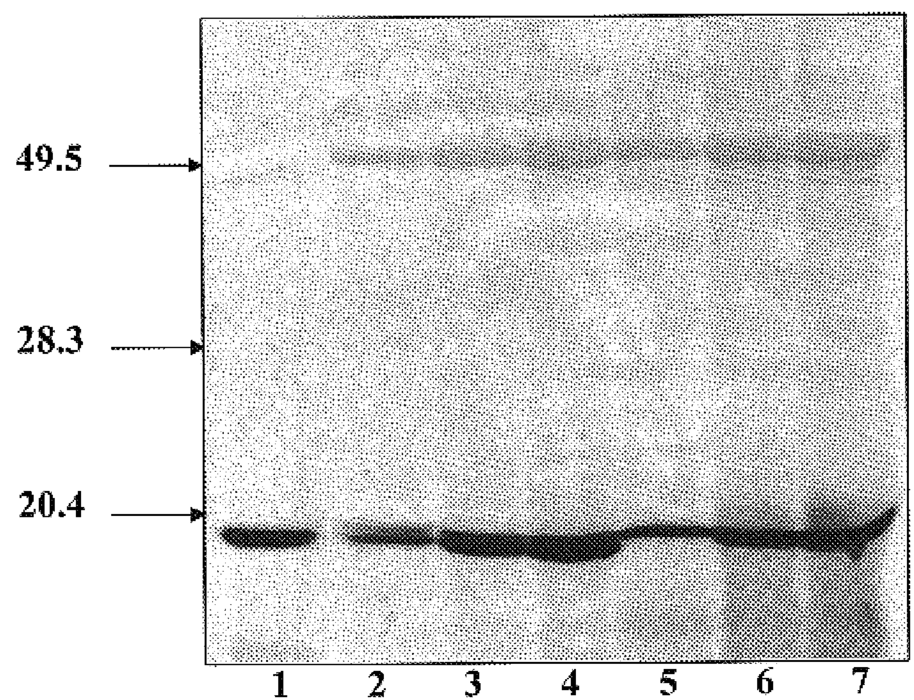
FIG. 18 is a purification analysis of pilin extracted from *P. aeruginosa* 1244/pLPS2 and *P. aeruginosa* 1244/pDIG4. The purity of pilin extractions from strain 1244/pLPS2 and strain 1244/pDIG4 were analyzed by a silver stained SDS-PAGE gel. Lane 1: *P. aeruginosa* 1244 (2.0 μg); lane 2: strain 1244/pLPS2 (4.3 μg); lane 3: strain 1244/pLPS2 (8.6 μg); lane 4: strain 1244/pLPS2 (12.9 μg); lane 5: strain 1244/pDIG[4] (3.4 μg); lane 6: strain 1244/pDIG4 (6.8 μg); lane 7: strain1244/pDIG4 (10.2 μg). Arrows indicate molecular weight markers (kDa).

These results were confirmed by mass analysis of the pilin produced in this experiment using matrix assisted laser desorption ionization (MALDI) mass spectrometry. Pili produced by *P. aeruginosa* 1244/pLPS2 was isolated from overnight plate cultures and purified as previously described (Castric, 1995). Purity of this preparation was determined by silver staining of an SDS-PAGE gel (FIG. 18). Using the Bradford Protein Assay with BSA as standard, it was determined that the sample contained approximately 1.7 mg of pilin. Once quantitated and the purity determined, the preparation was dialyzed overnight against 10 mM ammonium acetate to remove plyethylene glycol and salts, materials that would be deleterious to mass analysis.

The predicted mass of pilin produced by *P. aeruginosa* 1244 is 16,331 (15,648 of with is protein, with the remainder the 07 repeating unit). MALDI analysis of this pilin gives a value of 16,307 (+/−25). If the 011 repeating unit is being put on some of the strain 1244 pilin subunits, in the experiment described above, two distinctly different pilin masses would be seen. One would be 16,331 (representing 1244 pilin containing the 07 repeating unit) and the other 16,183 (15,648 for the pilin protein and the remainder for the 011 repeating unit). MALDI analysis of the *P. aeruginosa* 1244/pLPS2 pilin gave two peaks, 16,316 (+/−25) and 16,187 (+/−10). These results confirm that heterologous glycosylation is taking place, indicating that the glycosylation apparatus of this organism is extremely nonspecific.

The identification of two distinct pilin species indicates that separate pilin monomers are glycosylated with either the native or the PA103 O-antigen repeating unit. Altogether, these results show that the O-antigen biosynthetic pathway serves as the source of pilin glycosylation in *P. aeruginosa* 1244 and that pilO is non-specific for glycan substrate.

The results of the previous experiments unequivocally demonstrate that the O-antigen biosynthetic pathway is the metabolic source of pilin glycosylation in *P. aeruginosa* 1244. Because pilO glycan substrate recognition within *P. aeruginosa* appears to be non-specific, the following experiments were designed to determine the magnitude of pilO substrate specificity by identifying whether this protein was capable of utilizing the O-antigen from another species as the source for the pilin glycan.

Example 3

Figure 12:
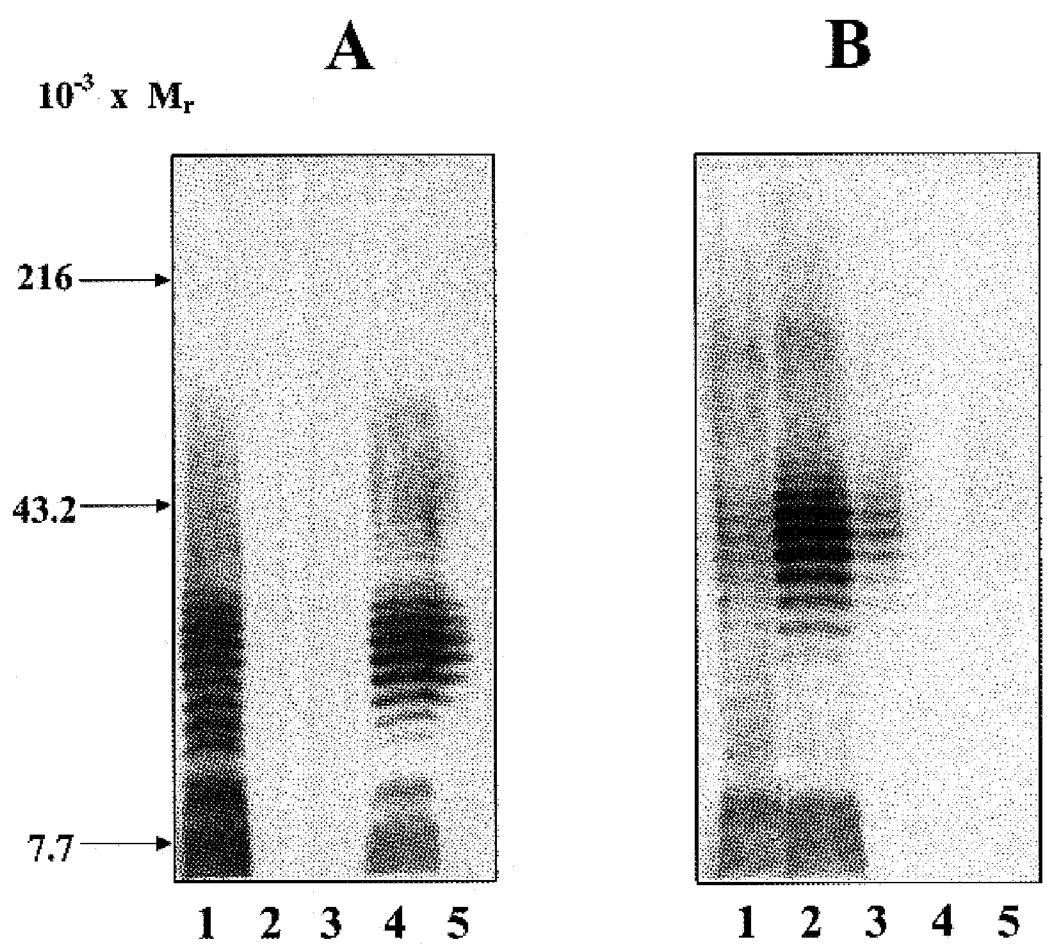
FIG. 12 is a western blot analysis of LPS derived from *P. aeruginosa* 1244/pDIG4. Panel A: lane 1: *P. aeruginosa* 1244/pDIG4; lane 2: *E. coli* HB101/pDIG4; lane 3: empty; lane 4: *P. aeruginosa* 1244; lane 5: *E. coli* HB101; Panel B: lane 1: *P. aeruginosa* 1244/pDIG4; lane 2: *E. coli* HB101/pDIG4; lane 3:empty; lane 4: *P. aeruginosa* 1244; lane 5: *E. coli* HB101; LPS was separated on a 12.5% SDS-PAGE gel and electroblotted to 0.2 μm nitrocellulose paper. Arrows indicate molecular weight markers (kDa). Panel A: analyzed with mAb 11.14; Panel B: analyzed with *E. coli* O157:H7 antiserum.
Figure 13:
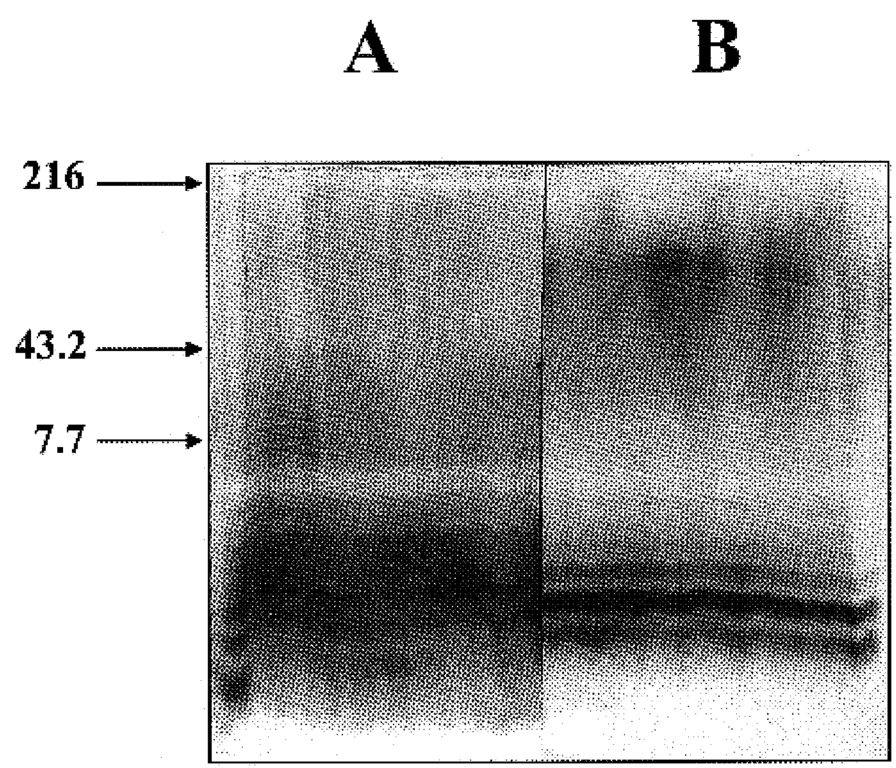
FIG. 13 is a western blot of LPS derived from *P. aeruginosa* 1244/pDIG4. LPS was separated in one lane on a 12.5% polyacrylamide gel and electroblotted to nitrocellulose paper. Arrows indicate molecular weight markers (kDa). Panel A: analyzed with *E. coli* O157:H7 antiserum; Panel B: analyzed with 1244 anti-LPS mAb 11.14.

The Cloned *E. coli* O157:H7 O-antigen Gene Cluster Acts as the O-antigen Source for *P. aeruginosa* 1244 LPS To identify whether the *E. coli* O157:H7 O-antigen could be expressed on *P. aeruginosa* 1244 LPS, pDIG4 one of the newly constructed cosmids, was transferred into *P. aeruginosa* 1244 and tested for O-antigen expression. As with *P. aeruginosa* 1244/pLPS2, two colonies from this mating were chosen for further analysis. Initially, confirmation of pDIG4 incorporation into *P. aeruginosa* 1244 was accomplished by performing a plasmid extraction on each Tc resistant colony (results not shown). The LPS from each 1244 strain harboring the pDIG4 plasmid was then extracted from overnight broth cultures, and tested by Western blot using mAb 11.14 (FIG. 12, panel A) and the *E. coli* O157:H7 specific antiserum (FIG. 12, panel B). This figure shows that strain 1244/pDIG4 produces the usual O-antigen ladder that is observed in the wild type 1244 strain when analyzed with mAb 11.14 (panel A, lane 4). In addition, there was no reaction seen in lanes 2 and 5, which contained *E. coli* HB101 /pDIG4 and *E. coli* HB101, respectively. In panel B of this figure, only the *P. aeruginosa* 1244 and *E. coli* HB101 strains harboring pDIG4 were capable of reacting with the O157:H7 antiserum (panel B, lanes 1 and 2, respectively). As with strain 1244/pLPS2, the LPS from strain 1244/pDIG4 were examined by Western blot to identify if this organism placed strain 1244 and O157:H7 O-antigen on separate LPS chains. Strain 1244/pDIG4 LPS was separated by SDS-PAGE using a preparative gel comb and analyzed by Western blot. One half of this blot was reacted with 11.14, while the other half was reacted with the O157:H7 antiserum. As seen in FIG. 13, the pattern of the O-antigen ladder is different when reacted with each antiserum. This indicates that strain 1244/pDIG4 is producing separate LPS molecules containing either strain 1244 O-antigen or the *E. coli* O157:H7 O-antigen.

Slide agglutination serum tests, using the *E. coli* O157:H7 antiserum, were performed on *P. aeruginosa* 1244/pDIG4 with *E. coli* HB101 and *E. coli* LE392/pDS300 serving as the negative and positive controls, respectively. In each case, a positive reaction was observed as shown by the distinctive clumping of *P. aeruginosa* 1244/pDIG4 cells tinder a dissection microscope (results not shown). These results confirm that *P. aeruginosa* 1244/pDIG4 is capable of expressing both wild type and the *E. coli* O157:H7 O-antigen on its LPS.

Example 4

The Cloned *E. coli* O157:H7 O-anitigen Gene Cluster Acts as a Pilin Glycan Source in *P. aeruginosa* 1244

Figure 14:
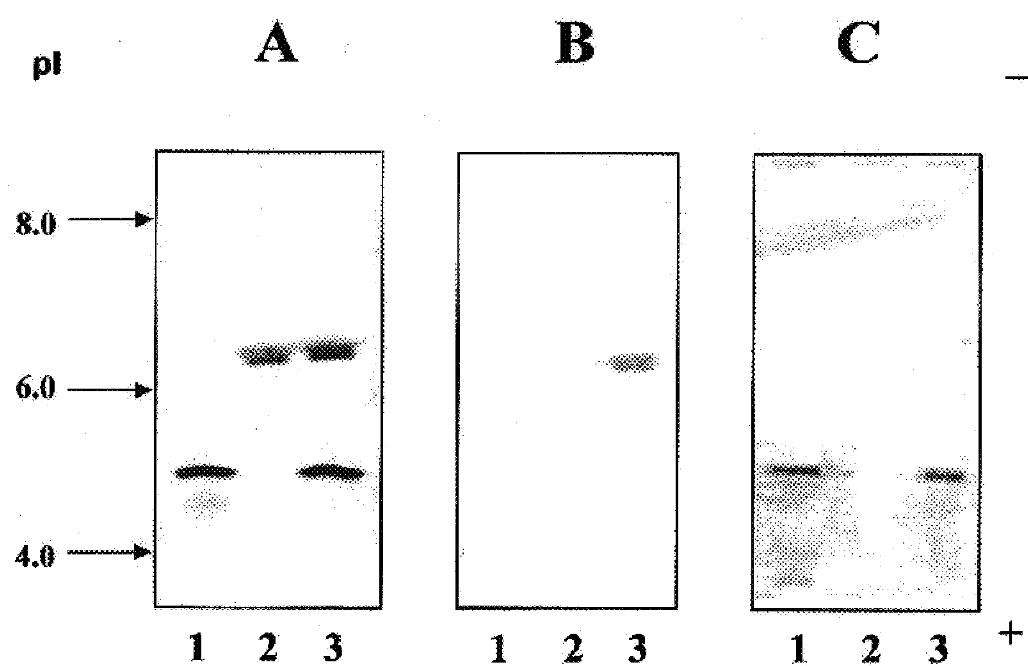
FIG. 14 shows results of isoelectric focusing of *P. aeruginosa* 1244/pDIG4 pili expressing the *E. coli* O157:H7 O-antigen. Panels A, B and C: lane 1: *P. aeruginosa* 1244 glycosylated pilin; lane 2: *P. aeruginosa* 1244 non-glycosylated pilin; lane 3: *P. aeruginosa* 1244/pDIG4; isoelectric focusing was performed using the LKB-Pharmacia Phastsystem as described by the manufacture specifications. Pilin was transferred to PVDF membrane by diffusion blotting. The pI value was determined by focusing standards on the same gel as the samples. Panel A: analyzed with mAb 6.45; Panel B: analyzed with *E. coli* O 157:H7 antiserum; Panel C: analyzed with mAb 11.14.

Once the expression of the *E. coli* O157:H7 O-antigen on *P. aeruginosa* 1244 LPS was confirmed, the pili of this strain were tested for the presence of the *E. coli* O157:H7 O-antigen. The pili from *P. aeruginosa* 1244/pDIG4 were extracted from overnight plate cultures and suspended in 1% BOG. Pilin samples were then separated by isoelectric focusing in a pH gradient of 3.5–9.5, transferred to PVDF membrane by diffusion blotting and reacted with mAb 6.45 (FIG. 14, panel A), the *E. coli* O157:H7 specific antiserum (FIG. 14, panel B), and mAb 11.14 (FIG. 14, panel C). The results of the focusing gel using mAb 6.45 reveal that *P. aeruginosa* 1244/pDIG4 is also generating two distinct types of pilin, an acidic and a neutral form (panel A, Lane 3). The acidic pilin from the recombinant organism focused to a pI of approximately 4.75, a charge consistent to that produced by wild type *P. aeruginosa* 1244 pilin (panel A, line 1). The neutral pilin from strain 1244/pDIG4 focused to a pI of 6.25, a value identical to that exhibited by non-glycosylated *P. aeruginosa* 1244 pilin (panel A, lane 2). When focusing was performed and analyzed with the *E. coli* O157:H7 antiserum, a reaction was only observed at pI 6.25 (panel B, lane 3), the same isoelectric point of the neutral pilin observed in panel A of this figure. When pilin was focused and analyzed with mAb 11.14, a reaction was only seen with pilin at pI 4.75 (panel C, lanes 1 and 3, respectively), a charge also exhibited by the pilin of wild type strain 1244.

Pili produced by *P. aeruginosa* 1244/pDIG4 were produced using the procedure described in Example 2. Purity was determined (FIG. 18), while protein quantitation indicated the presence of approximately 1.4 mg protein. MALDI analysis of this material is currently being carried out.

Together, these results indicate that the *E. coli* O157:H7 O-antigen biosynthetic pathway is the source of the plain glycan. As with strain 1244/pLPS2, it is apparent that strain 1244/pDIG4 is producing two distinct species of pilin. This indicates that pilO is glycosylating separate strain 1244 pilin monomers with either the wild type or the *E. coli* O157:H7 O-antigen, an unusual occurrence considering the structural dissimilarity between the two O-antigen repeating units. Therefore, these results show that pilO is non-specific for glycan recognition.

Example 5

Characterization of Pili Containing the Mixed Glycan

Usually, pilin is obtained in small quantities from overnight plate cultures because *P. aeruginosa* has been shown to suppress piliation while shaking in broth culture (Yee and Castric, unpublished observations). This laboratory has shown that *P. aeruginosa* 1244N3 (Ramphal et al., 1991), a mutant which is unable to produce pilin due to an inactivated rpoN gene, lacks pili shake suppression in broth culture when complemented with pPAC46, a plasmid containing the strain 1244 pilA and pilO genes under the control of a tac promoter (Yee and Castric, unpublished observations). When grown in the presence of IPTG, this organism is capable of hype-expressing glycosylated strain 1244 pili (Yee and Castric, unpublished observations). It is conceivable that an rpoN mutant strain of *P. aeruginosa* 1244, when complemented with pPAC46 and either pDIG4 or pLPS2, can produce a large amount of pilin with either the *P. aeruginosa* serotype O11 or *E. coli* O157:H7 glycan. This would allow enough glycosylated pilin to be isolated for structural analysis as well as for future vaccine construction. Unfortunately, *P. aeruginosa* 1244N3 cannot be used for these experiments because the rpoN mutation is marked with a tetracycline cassette, the same selectable marker as pDIG4 and pLPS2. Therefore, the isolation of a rpoN mutant with a marker other than tetracycline was performed using a gene replacement technique in *P. aeruginosa* that was first described by Schweizer (1992):

1. Isolation of an rpoN Mutant Strain of *P. aeruginosa* 1244 a. Allele Replacement of the rpoN Gene in *P. aeruginosa* 1244

Figure 15:
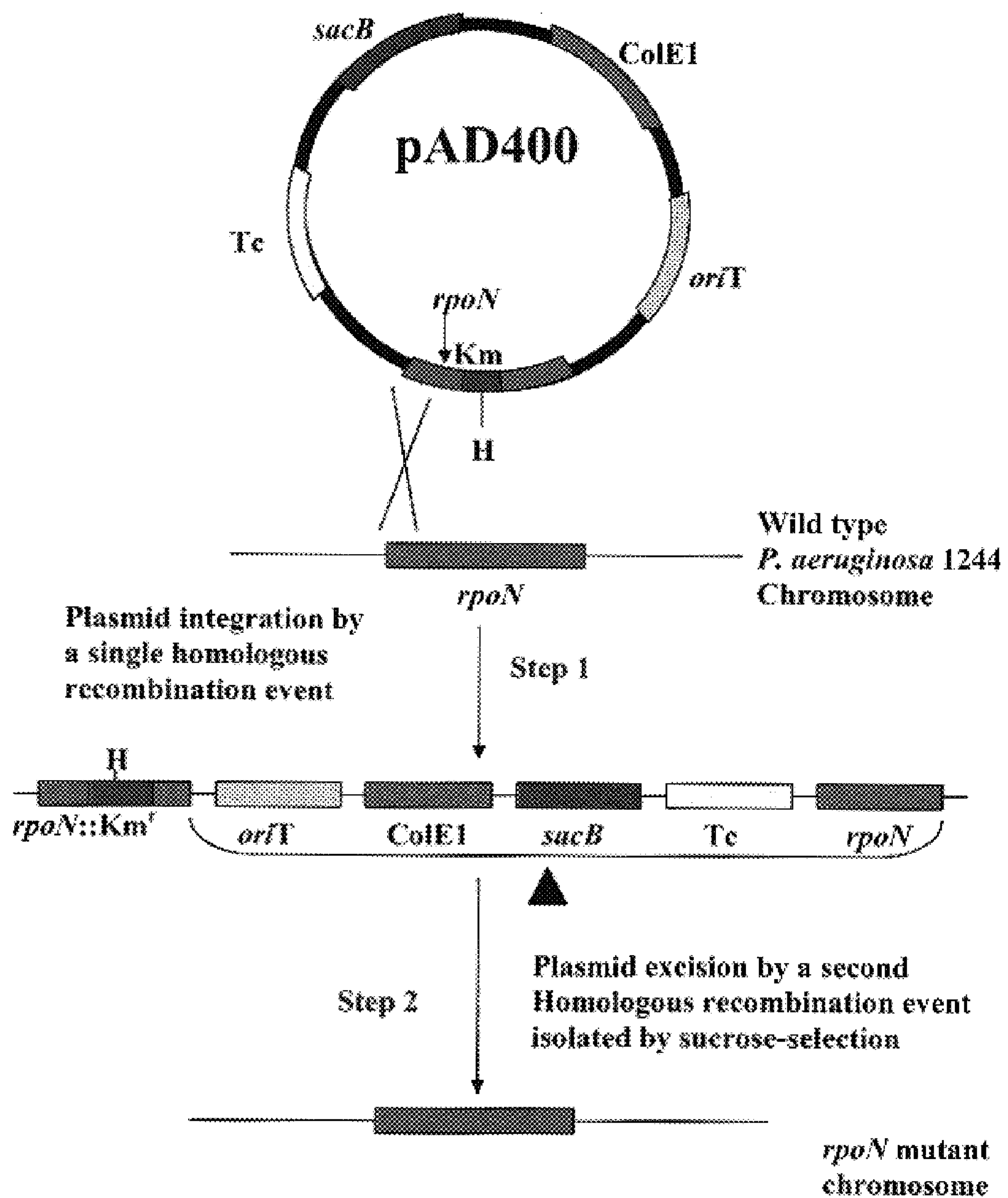
FIG. 15 depicts allele replacement of the rpoN gene in *P. aeruginosa* 1244. Step 1 of this diagram depicts the integration of pAD400 into the *P. aeruginosa* 1244 chromosome at the wild type rpoN gene, forming a merodiploid. This strain is now $Km^r Tc^r$ and $sucrose^s$. Step 2 depicts the excision of plasmid DNA by homologous recombination that is promoted by selecting for sucrose and Km resistance. The rpoN gene has now been replaced by the mutated rpoN allele, resulting in an organism that contains a Km insertional mutation in the rpoN gene.

In order to perform the rpoN allele replacement in *P. aeruginosa* 1244, pAD400 was chosen and conjugally transferred into *P. aeruginosa* 1244 by a triparental mating system. The mating mix was selected on agar plates containing Km, to identify strain 1244 plasmid integrants, Spectinomycin, to selected against any *E. coli* organisms, and 7.5% sucrose to isolate strains where plasmid excision had occurred. Colonies began to appear after 18 hours of incubation at 37(C and were allowed to grow for an additional 24 to 28 hours at room temperature until they reached adequate size for colony immmunoblotting. Following the incubation period, a colony immunoblot blot was performed for each mating mix plate and reacted with mAb 6.45 to test for pilin production (results not shown). A total of 169 colonies were isolated that did not react with mAb 6.45 and should represent those cells in which allele replacement of the rpoN gene had occurred (FIG. 15). Four of these colonies were chosen for further analysis and named *P. aeruginosa* 1244O7, 1244Q3, 1244Q13 and 1244R10.

b. Phenotypic Analysis of the Putative rpoN Mutants

Figure 16:
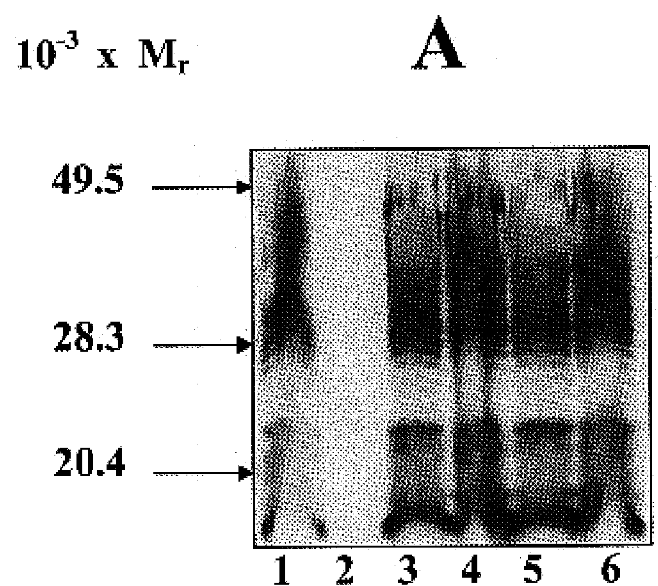
FIG. 16 is a phenotypic analysis of the putative rpoN mutants by western blot. Panel A and B: lane 1: *P. aeruginosa* 1244; lane 2: *E. coli* HB101; lane 3: 1244O7; lane 4: 1244Q3; lane 5: 1244Q13; lane 6: 1244R10. Panel A was separated on a 12.5% polyacrylamide gel, while panel B was separated on a 13.75% polyacrylamide gel. Both gels were electroblotted to nitrocellulose paper. Arrows indicate molecular weight markers (kDa). Panel A: analyzed with 1244 anti-LPS mAb 11.14. Panel B: analyzed with 1244 anti-pilin mAb 6.45.
Figure 16:
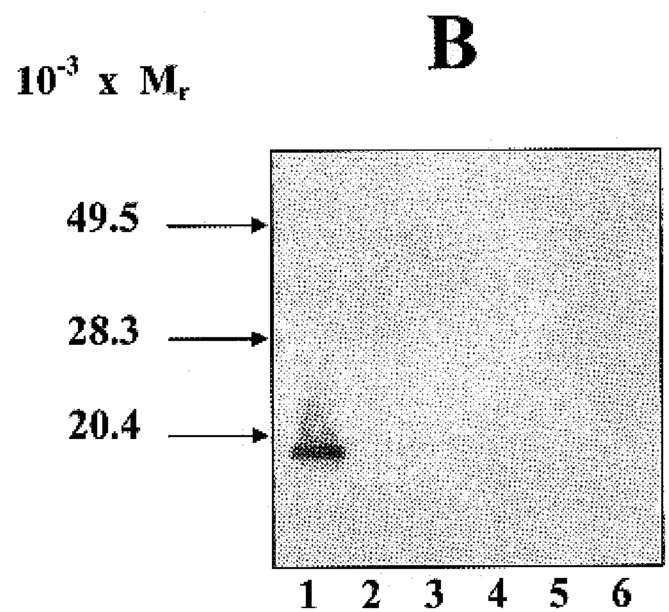

Since the rpoN::Km$^r$ cassette was derived from pAD400, each strain was tested for Tc sensitivity to ensure plasmid excision. All 4 strains were Tc$^s$. The LPS from each putative rpoN mutant was then extracted, as described earlier, from overnight broth cultures and analyzed by Western blot using strain 1244 anti-LPS mAb 11.14 to ensure each strain was derived from *P. aeruginosa* 1244. As illustrated in FIG. 16, panel A, all 4 putative rpoN mutants produced strain 1244 serotype specific O-antigen (panel A, lanes 3–6) similar to the wild type strain 1244 (panel A, lane 1). These results indicate that all four of the putative rpoN mutant strains are derived from wild type strain 1244.

To confirm the loss of pilin production, whole cell extracts from each putative rpoN mutant was obtained from overnight plate cultures and analyzed by Western blot using anti-pilin mAb 6.45. As seen in FIG. 16, panel B, there was no reaction observed with any of the four putative rpoN mutants (lanes 3–6) as was observed with the wild type strain 1244 (lane 1). These results show that the putative rpoN mutants are not producing pilin and indicate that the rpoN gene has been successfully replaced with the mutated rpoN allele.

c. Southern Blot Analysis of the Putative rpoN Mutant Strain 1244Q13

Figure 17A:
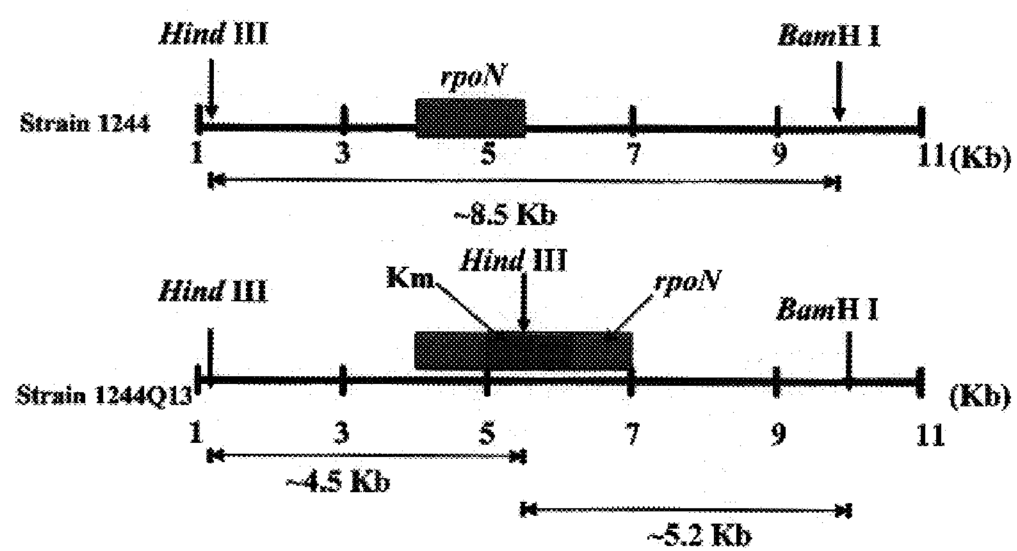
FIG. 17 is a genomic analysis of the rpoN mutant strain, 1244Q13. (a) Analysis of strain 1244 genomic DNA revealed Hind III and BamH I restriction sequences that will result in the formation of an 8.5 Kb DNA fragment after digestion with both enzymes. If the kanamycin cassette has been inserted into the strain 1244 chromosome at the rpoN locus, Hind III and BamH I digestion will result in the isolation of 4.5 and 5.2 Kb DNA fragments. (b) Panel A: lane 1: biotinylated lambda Hind III digest; lane 2: strain 1244 Hind III and BamH I genomic digestion; lane 3: strain 1244Q13 genomic digestion with Hind III and BamH I; Panel B: southern blot analysis of genomic digests using the rpoN allele as a probe. (c) PCR amplification of strain 1244 genomic DNA (lane 1) and 1244Q13 genomic DNA (lane 2) using rpoN specific primers. Arrows indicate DNA size markers (Kb).
Figure 17B:
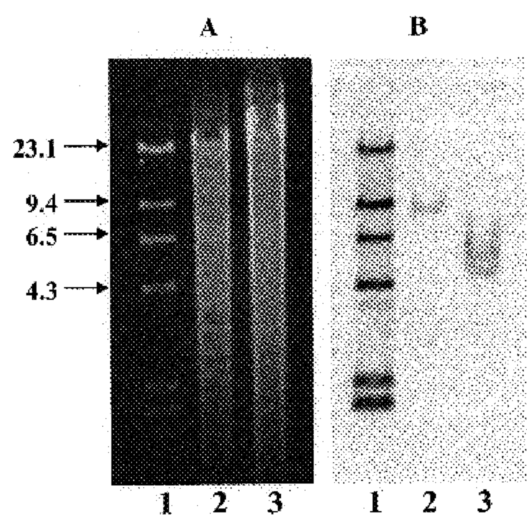
Figure 17C:
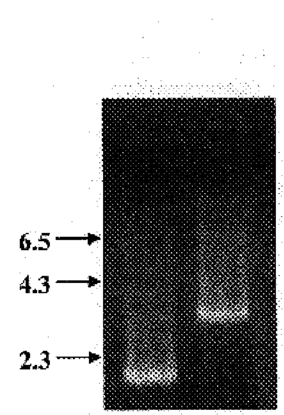

To confirm that the wild type rpoN allele had been replaced with the mutated rpoN gene, a southern blot was performed on the putative rpoN mutant, 1244Q13. Analysis of strain 1244 genomic DNA revealed Hind III and BamH I restriction sequences located approximately 3 Kb and 4.2 Kb upstream and downstream on the rpoN gene, respectively (FIG. 17*a*). Therefore, simultaneous digestion with both restriction enzymes should result in an approximately 8.5 Kb DNA fragment (FIG. 17*a*). In addition, the Km$^r$ cassette used to mutate the rpoN gene contains an internal Hind III site. If allele exchange had occurred, restriction digest of strain 1244Q13 genomic DNA with Hind III and BamH I should reveal 2 DNA fragments of approximately 4.5 and 5.2 Kb (FIG. 17*a*). FIG. 17*b* shows the southern blot of strain 1244 and 1244Q13 genomic DNA that was digested with Hind III and BamH I (panel A, lanes 2 and 3, respectively) and probed with a biotinylated rpoN gene isolated by PCR (panel B, lanes 2 and 3, respectively). The probe reacted with an 8.6 Kb DNA fragment in the strain 1244 digest (panel B, lane 2), and with 2 DNA fragments of approximately 4.5 and 5.2 Kb in the 1244Q13 digest (panel B, lane 3). In addition, PCR amplification using rpoN specific primers with strain 1244 and 1244Q13 genomic DNA revealed a 2.7 Kb DNA fragment for 1244Q13 (FIG. 17*c*, lane 2) compared to the 1.5 Kb DNA for 1244 (FIG. 17*c*, lane 1). Together, these results are consistent with the insertion of the 1.2 Kb Km$^r$ cassette into the wild type rpoN allele. 1244Q13 is therefore a rpoN::Km$^r$ mutant strain that is unable to produce pilin.

Example 6

Covalent Attachment of Isolated *P. Aeruginosa* 1244 Pilin Aminoglycan with Ovalbumin.

The aminoglycan fraction from pure *P. aeruginosa* 1244 pilin was isolated as described previously (Castric, P. et al. 2001. J. Biol. Chem. 276:26479–26485). Briefly, this involved complete proteolysis of from 10 to 20 mg of pure pili. This treatment released the glycan covalently attached to a serine residue (the pilin residue to which it was attached). The aminoglycan was purified by gel filtration (Sephadex G-25) and thin layer chromatography.

The following procedure was used to attach this molecule to ovalbumin through the amino group of the aminoglycan: 7.9 mg (175 nmol) of ovalbumin was dissolved in 2.0 ml of Phosphate Buffered Saline (PBS) in a 10 ml beaker. To this was added 25 nmol aminoglycan. 2.0 ml of 0.2% glutaraldehyde in PBS was slowly added dropwise. This material was allowed to stir for 1 hour at room temperature, at which time 0.5 ml of 1.0M glycine was added to quench the cross linking reaction. The reaction mixture was exhaustively dialyzed and stored frozen.

Figure 19:
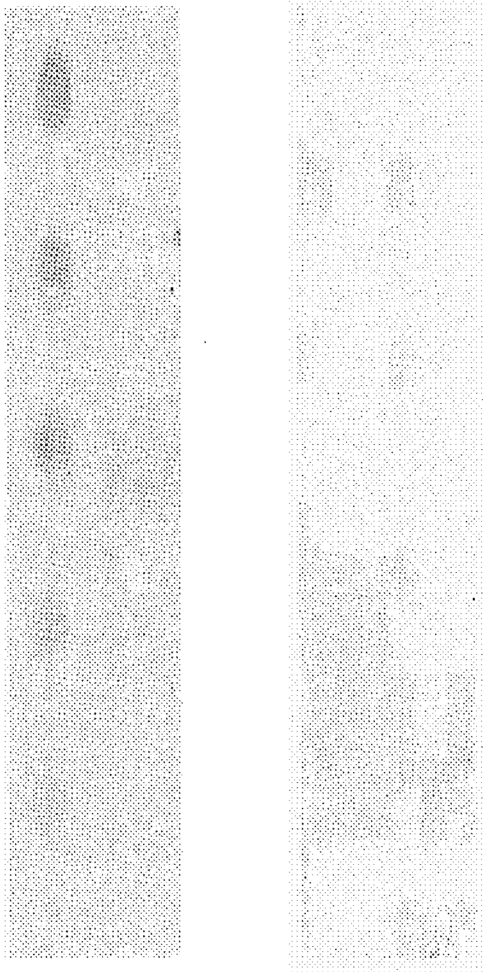
FIG. 19 shows the reaction of ovalbumin-pilin aminoglycan conjugate with glycan-specific monoclonal 11.14. Serial dilutions of ovalbumin-pilin aminoglycan conjugate (lanes 1 and 3) and unreacted ovalbumin (lanes 2 and 4) were spotted on nitrocellulose paper. Each protein had an initial concentration of 2.0 mg/ml. The spotted paper was probed with either pilin glycan-specific monoclonal 11.14 or pilin protein-specific monoclonal 5.44.

The presence of covalently attached aminoglycan was tested by dotblot using glycan-specific monoclonal 11.14 as probe (FIG. 19). These results show that the conjugated protein has acquired the pilin glycan epitope, and indicate that it is possible to attach the isolated pilin glycan to a carrier protein other than pilin.

Whereas particular embodiments of this invention have been described above for purposes of illustration, it will be evident to those skilled in the art that numerous variations of the details of the present invention may be made without departing from the invention as defined in the appending claims.

What is claimed is:

1. A method of eliciting an immune response against a Gram-negative bacterial infection in a vertebrate animal comprising:

introducing a vector containing genes encoding the O-antigen of a Gram-negative bacterium into a strain of *Pseudomonas aeruginosa* containing the pilO gene such that the O-antigen is expressed in said *Pseudomonas aeruginosa* and said pilin is glycosylated with said O-antigen of said Gram-negative bacterium;

isolating said glycosylated pilin; and administering said glycosylated pilin to said vertebrate animal, in a pharmaceutically suitable carrier.

2. The method of claim 1, wherein said strain of *P. aeruginosa* is strain 1244.

3. The method of claim 1, wherein said Gram-negative bacterium is *E. coli.*

4. The method of claim 1, wherein said Gram-negative bacterium is *P. aeruginosa* strain 011.

5. The method of claim 1, further comprising isolating antibodies produced in response to administration of said glycosylated pilin in said vertebrate animals.

6. The method of claim 5, further comprising administering said antibodies to a vertebrate animal suffering from said Gram-negative bacterial infection, to provide passive immunity against said infection.

7. The method of claim 5, further comprising:

(a) contacting a sample from a vertebrate animal thought to have a Gram-negative bacterial infection with said antibodies; and (b) detecting the presence or absence of said Gram-negative bacterial infection by detecting the presence or absence of a complex formed between said O-antigen and said antibodies specific therefore.

8. A method of eliciting an immune response in a vertebrate animal having an infection from a Gram-negative bacteria comprising:

administering glycosylated pilin to said vertebrate animal in a pharmaceutically acceptable carrier, said glycosylated pilin containing an O-antigen derived from a Gram-negative bacterium which is not a strain of *Pseudomonas aeruginosa* containing the pilO gene.

9. The method of claim 1, wherein said immune response is protective.

10. The method of claim 8, wherein said immune response is protective.

* * * * *

UNITED STATES PATENT AND TRADEMARK OFFICE

CERTIFICATE OF CORRECTION

PATENT NO. : 7,135,175 B2
APPLICATION NO. : 11/192962
DATED : November 14, 2006
INVENTOR(S) : Peter A. Castric It is certified that error appears in the above-identified patent and that said Letters Patent is hereby corrected as shown below:

Front page, (75) Inventor: “Paul A. Castric” should read --Peter A. Castric--

Column 1, line 66, “lipopolysacciaride” should read --lipopolysaccharide--

Column 2, lines 56 and 57, “pilO” should read --*pilO*--

Column 2, line 62, “cosinid” should read --cosmid--

Column 3, line 7, “homologous” should read --Homologous--

Column 3, line 63, “pilA” should read --*pilA*--

Column 3, line 65, “pilO” should read --*pilO*--

Column 4, line 3, “pilO” should read --*pilO*--

Column 4, line 24, “pilO” should read --*pilO*--

Column 6, line 9, “rpoN” should read --*rpoN*--

Column 6, line 12, “pA:D99” should read --*pAD99*--

Column 6, line 12, “rpoN” should read --*rpoN*--

Column 6, line 13, “Kpn I” should read --*Kpn I*--

Column 6, line 15, “rpoN” should read --*rpoN*--

Column 6, line 18, “Pst I” should read --*Pst I*--

Column 6, line 21, “rpoN” should read --*rpoN*--

Column 6, line 24, “Pst I” should read --*Pst I*--

Column 6, line 27, “rpoN” should read --*rpoN*--

Column 6, line 28, “rpoN” should read --*rpoN*--

Column 6, line 29, “Kpn I” should read --*Kpn I*--

Column 7, line 23, “rpoN” should read --*rpoN*--

UNITED STATES PATENT AND TRADEMARK OFFICE

CERTIFICATE OF CORRECTION

PATENT NO. : 7,135,175 B2
APPLICATION NO. : 11/192962
DATED : November 14, 2006
INVENTOR(S) : Peter A. Castric It is certified that error appears in the above-identified patent and that said Letters Patent is hereby corrected as shown below:

Column 7, line 26, "rpoN" should read --*rpoN*--

Column 7, line 30, "rpoN" should read --*rpoN*--

Column 7, line 32, "rpoN" should read --*rpoN*--

Column 7, line 33, "rpoN" should read --*rpoN*--

Column 7, line 44, "rpoN" should read --*rpoN*--

Column 7, line 45, "Hind" should read --*Hind*--

Column 7, line 49, "Hind" should read --*Hind*--

Column 7, line 49, "rpoN" should read --*rpoN*--

Column 7, line 50, "Hind" should read --*Hind*--

Column 7, line 50, "Bam" should read --*Bam*--

Column 7, line 52, "Hind" should read --*Hind*--

Column 7, line 53, "Hind" should read --*Hind*--

Column 7, line 53, "Bam" should read --*Bam*--

Column 7, line 54, "Bam" should read --*Bam*--

Column 7, line 55, "rpoN" should read --*rpoN*--

Column 7, line 57, "rpoN" should read --*rpoN*--

Column 7, line 67, "1244/pDIG$^{4}$" should read --1244/pDIG4--

Column 7, line 18, "pilO" should read --*pilO*--

Column 7, line 23, "pilO" should read --*pilO*--

Column 10, line 63, "(oriR)" should read --(*ori*R)--

Column 10, line 64, "(oriT)" should read --(*ori*T)--

UNITED STATES PATENT AND TRADEMARK OFFICE

CERTIFICATE OF CORRECTION

PATENT NO. : 7,135,175 B2
APPLICATION NO. : 11/192962
DATED : November 14, 2006
INVENTOR(S) : Peter A. Castric It is certified that error appears in the above-identified patent and that said Letters Patent is hereby corrected as shown below:

Column 11, line 1, "(tra)" should read --(*tra*)--

Column 11, line 3, "Ira" should read --*tra*--

Column 11, line 4, "(tra)" should read --(*tra*)--

Column 11, line 5, "oriT" should read --*ori*T--

Table 1, column 11, line 63, "rpoN" should read --*rpoN*--

Table 1, column 12, line 22, "PstI" should read --*PstI*--

Table 1, column 12, line 24, "rpoN" should read --*rpoN*--

Table 1, column 12, line 27, "PstI" should read --*PstI*--

Table 1, column 12, line 38, "PstI" should read --*PstI*--

Table 1, column 12, line 41, "rpoN" should read --*rpoN*--

Table 1, column 12, line 41, "LB $Gm^{10}Tc^{10}$" should read --LB $\underline{Gm^{10}Tc^{10}}$--

Table 1, column 12, line 43, "rpoN" should read --*rpoN*--

Table 1, column 12, line 45, "rpoN" should read --*rpoN*--

Table 1, column 12, line 47, "rpoN" should read --*rpoN*--

Column 13, line 3, "supernat ant" should read --supernatant--

Column 14, line 10, "0.54" should read --0.53--

Column 16, line 38, "Hind" should read --*Hind*--

Column 16, line 51, "( 13.5 mM EDTA, 50" should read --(13.5 mM EDTA, 50--

Column 17, line 45, "EcoR" should read --*EcoR*--

Column 17, line 50, "EcoR" should read --*EcoR*--

Column 18, line 8, "EcoR" should read --*EcoR*--

UNITED STATES PATENT AND TRADEMARK OFFICE

CERTIFICATE OF CORRECTION

PATENT NO. : 7,135,175 B2
APPLICATION NO. : 11/192962
DATED : November 14, 2006
INVENTOR(S) : Peter A. Castric It is certified that error appears in the above-identified patent and that said Letters Patent is hereby corrected as shown below:

Column 18, line 18, “EcoR” should read --*EcoR*--

Column 18, line 19, “EcoR” should read --*EcoR*--

Column 19, line 8, “oriT” should read --*ori*T--

Column 19, line 8, “oriT” should read --*ori*T--

Column 19, line 9, “sacB” should read --*sacB*--

Column 19, line 9, “genes” should read --gene--

Column 19, line 12, “sacB” should read --*sacB*--

Column 19, line 19, “oriT” should read --*ori*T--

Column 19, line 25, “acquistion” should read --acquisition--

Column 19, line 33, “rpoN” should read --*rpoN*--

Column 19, line 34, “rpoN” should read --*rpoN*--

Column 19, line 38, “rpoN” should read --*rpoN*--

Column 19, line 39, “Pst I” should read --*Pst I*--

Column 19, line 40, “Pst I” should read --*Pst I*--

Column 19, line 45, “Pst I” should read --*Pst I*---

Column 19, line 46, “EcoR” should read --*EcoR*--

Column 19, line 46, “Hind” should read --*Hind*--

Column 19, line 47, “EcoR” should read --*EcoR*--

Column 19, line 48, “Hind” should read --*Hind*--

Column 19, line 48, “Pst I” should read --*Pst I*--

Column 19, line 49, “rpoN” should read --*rpoN*--

UNITED STATES PATENT AND TRADEMARK OFFICE

CERTIFICATE OF CORRECTION

PATENT NO. : 7,135,175 B2
APPLICATION NO. : 11/192962
DATED : November 14, 2006
INVENTOR(S) : Peter A. Castric It is certified that error appears in the above-identified patent and that said Letters Patent is hereby corrected as shown below:

Column 19, line 51, "EcoR" should read --*EcoR*--

Column 19, line 52, "Hind" should read --*Hind*--

Column 19, line 52, "rpoN" should read --*rpoN*--

Column 19, line 54, "Hind" should read --*Hind*--

Column 19, line 58, "Hind" should read --*Hind*--

Column 19, line 61, "rpoN" should read --*rpoN*--

Column 19, line 61, "Kpn I" should read --*Kpn I*--

Column 19, line 64, "Pst I" should read --*Pst I*--

Column 19, line 64, "rpoN" should read --*rpoN*--

Column 19, line 65, "Kpn" should read --*Kpn*--

Column 20, line 1, "rpoN" should read --*rpoN*--

Column 20, line 2, "Pst I" should read --*Pst I*--

Column 20, line 3, "preformed" should read --performed--

Column 20, line 4, "Pst I" should read --*Pst I*--

Column 20, line 11, "Pst I" should read --*Pst I*--

Column 20, line 12, "Pst I" should read --*Pst I*--

Column 20, line 14, "rpoN" should read --*rpoN*--

Column 20, line 21, "Pst I" should read --*Pst I*--

Column 20, line 21, "Kpn I" should read --*Kpn I*--

Column 20, line 21, "EcoR" should read --*EcoR*--

Column 20, line 22, "rpoN" should read --*rpoN*--

UNITED STATES PATENT AND TRADEMARK OFFICE

CERTIFICATE OF CORRECTION

PATENT NO. : 7,135,175 B2
APPLICATION NO. : 11/192962
DATED : November 14, 2006
INVENTOR(S) : Peter A. Castric It is certified that error appears in the above-identified patent and that said Letters Patent is hereby corrected as shown below:

Column 20, line 32, “rpoN” should read --*rpoN*--

Column 20, line 32, “rpoN” should read --*rpoN*--

Column 20, line 33, “Kpn I” should read --*Kpn I*--

Column 20, line 46, “Ampg” should read --Amp®--

Column 21, line 38, “rpoN” should read --*rpoN*--

Column 21, line 42, “rpoN” should read --*rpoN*--

Column 21, line 52, “Bam” should read --*Bam*--

Column 21, line 52, “Hind” should read --*Hind*--

Column 23, line 49, “pill” should read --pili--

Column 24, line 28, “with” should read --which--

Column 24, line 46, “pilO” should read --*pilO*--

Column 24, line 50, “pilO” should read --*pilO*--

Column 24, line 53, “pilO” should read --*pilO*--

Column 25, line 33, “tinder” should read --under--

Column 26, line 13, “pilO” should read --*pilO*--

Column 26, line 17, “pilO” should read --*pilO*--

Column 26, line 30, “rpoN” should read --*rpoN*--

Column 26, line 32, “pilA” should read --*pilA*--

Column 26, line 32, “pilO” should read --*pilO*--

Column 26, line 32, “tac” should read --*tac*--

Column 26, line 37, “rpoN” should read --*rpoN*--

UNITED STATES PATENT AND TRADEMARK OFFICE

CERTIFICATE OF CORRECTION

PATENT NO. : 7,135,175 B2
APPLICATION NO. : 11/192962
DATED : November 14, 2006
INVENTOR(S) : Peter A. Castric It is certified that error appears in the above-identified patent and that said Letters Patent is hereby corrected as shown below:

Column 26, line 44, "rpoN" should read --*rpoN*--

Column 26, line 46, "rpoN" should read --*rpoN*--

Column 26, line 50, "rpoN" should read --*rpoN*--

Column 26, line 52, "rpoN" should read --*rpoN*--
Column 26, line 54, "rpoN" should read --*rpoN*--

Column 26, line 62, "37 (C" should read -- 37°C--

Column 27, line 3, "rpoN" should read --*rpoN*--

Column 27, line 6, "rpoN" should read --*rpoN*--

Column 27, line 7, "rpoN" should read --*rpoN*--

Column 27, line 10, "rpoN" should read --*rpoN*--

Column 27, line 14, "rpoN" should read --*rpoN*--

Column 27, line 17, "rpoN" should read --*rpoN*--

Column 27, line 23, "rpoN" should read --*rpoN*--

Column 27, line 26, "rpoN" should read --*rpoN*--

Column 27, line 27, "rpoN" should read --*rpoN*--

Column 27, line 28, "rpoN" should read --*rpoN*--

Column 27, line 29, "rpoN" should read --*rpoN*--

Column 27, line 31, "rpoN" should read --*rpoN*--

Column 27, line 32, "rpoN" should read --*rpoN*--

Column 27, line 34, "Hind" should read --*Hind*--

Column 27, line 34, "Bam" should read --*Bam*--

UNITED STATES PATENT AND TRADEMARK OFFICE

CERTIFICATE OF CORRECTION

PATENT NO. : 7,135,175 B2
APPLICATION NO. : 11/192962
DATED : November 14, 2006
INVENTOR(S) : Peter A. Castric It is certified that error appears in the above-identified patent and that said Letters Patent is hereby corrected as shown below:

Column 27, line 36, "rpoN" should read --*rpoN*--

Column 27, line 40, "rpoN" should read --*rpoN*--

Column 27, line 42, "Hind" should read --*Hind*--

Column 27, line 46, "Hind" should read --*Hind*--

Column 27, line 46, "Bam" should read --*Bam*--

Column 27, line 47, "rpoN" should read --*rpoN*--

Column 28, line 5, "rpoN" should read --*rpoN*--

Column 28, line 10, "rpoN" should read --*rpoN*--

Column 28, line 11, "rpoN" should read --*rpoN*--

Claim 8, Column 32, line 28, "pilO" should read --*pilO*--

Signed and Sealed this

Seventeenth Day of April, 2007

JON W. DUDAS
*Director of the United States Patent and Trademark Office*